US012806014B2

(12) United States Patent
Han et al.

(10) Patent No.: US 12,806,014 B2
(45) Date of Patent: Nov. 24, 2026

(54) ARTIFICIAL CHORDAE

(71) Applicant: EDWARDS LIFESCIENCES CORPORATION, Irvine, CA (US)

(72) Inventors: Jingjia Han, Irvine, CA (US); Ling Zhou, Bellevue, WA (US); Holly Kung Jung Hsu, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 373 days.

(21) Appl. No.: 18/417,168

(22) Filed: Jan. 19, 2024

(65) Prior Publication Data

US 2024/0148506 A1 May 9, 2024

Related U.S. Application Data

(63) Continuation of application No. PCT/US2022/036453, filed on Jul. 8, 2022.

(Continued)

(51) Int. Cl.

*A61F 2/24* (2006.01)
*A61L 27/36* (2006.01)
*A61L 27/58* (2006.01)

(52) U.S. Cl.

CPC ........ *A61F 2/2457* (2013.01); *A61L 27/3625* (2013.01); *A61L 27/3633* (2013.01);

(Continued)

(58) Field of Classification Search

CPC ............ A61F 2/2457; A61F 2210/0004; A61F 2210/0076; A61F 2220/0075;

(Continued)

(56) References Cited

U.S. PATENT DOCUMENTS

| | | | |
|---|---|---|---|
| 3,131,957 A | 5/1964 | Musto | |
| 3,752,516 A | 8/1973 | Mumma | |

(Continued)

FOREIGN PATENT DOCUMENTS

| | | |
|---|---|---|
| EP | 0791330 A3 | 11/1997 |
| EP | 3505077 A1 | 7/2019 |

(Continued)

OTHER PUBLICATIONS

Alfieri, 0. et al., "The double-orifice technique in mitral valve repair: a +A198:A225simple solution for complex problems," (2001) J. Thorne. Cardiovasc. Surg., 122(4):674-681.

(Continued)

*Primary Examiner* — Bruce E Snow
(74) *Attorney, Agent, or Firm* — Chang and Hale LLP

(57) ABSTRACT

An artificial chordae system can comprise a surgical pad configured to be externally positioned over an opening formed in a portion of a heart wall adjacent to a heart ventricle, and a tether comprising a cord and a tissue ingrowth promoting coating over at least a portion of the cord, the tether comprising a distal portion being configured to couple a heart valve leaflet and a proximal portion being coupled to the surgical pad. The tether can be dimensioned to extend from the heart valve leaflet through the heart ventricle to the opening in the heart wall, and through the opening in the heart wall to the surgical pad. The tissue ingrowth promoting coating can comprise a protein and be configured to promote native tissue growth over the cord to provide regenerated native tissue over the tether for coupling the heart valve leaflet to the heart wall.

20 Claims, 12 Drawing Sheets

Related U.S. Application Data

(60) Provisional application No. 63/223,721, filed on Jul. 20, 2021.

(52) U.S. Cl.
CPC ....... *A61L 27/58* (2013.01); *A61F 2210/0004* (2013.01); *A61F 2210/0076* (2013.01); *A61F 2220/0075* (2013.01); *A61L 2300/412* (2013.01); *A61L 2430/20* (2013.01)

(58) Field of Classification Search
CPC ..... A61F 2220/0008; A61F 2250/0051; A61L 27/3625; A61L 27/3633; A61L 27/58; A61L 2300/412; A61L 2430/20
See application file for complete search history.

(56) References Cited

U.S. PATENT DOCUMENTS

| | | | |
|---|---|---|---|
| 4,403,797 | A | 9/1983 | Ragland, Jr. |
| 4,662,376 | A | 5/1987 | Belanger |
| 4,807,625 | A | 2/1989 | Singleton |
| 5,144,961 | A | 9/1992 | Chen et al. |
| 5,147,316 | A | 9/1992 | Castillenti |
| 5,312,423 | A | 5/1994 | Rosenbluth et al. |
| 5,391,176 | A | 2/1995 | de la Torre |
| 5,405,352 | A | 4/1995 | Weston |
| 5,454,821 | A | 10/1995 | Harm et al. |
| 5,472,446 | A | 12/1995 | de la Torre |
| 5,507,754 | A | 4/1996 | Green et al. |
| 5,527,323 | A | 6/1996 | Jervis et al. |
| 5,554,184 | A | 9/1996 | Machiraju |
| 5,626,614 | A | 5/1997 | Hart |
| 5,643,293 | A | 7/1997 | Kogasaka et al. |
| 5,681,331 | A | 10/1997 | de la Torre et al. |
| 5,716,368 | A | 2/1998 | de la Torre et al. |
| 5,727,569 | A | 3/1998 | Benetti et al. |
| 5,728,109 | A | 3/1998 | Schulze et al. |
| 5,746,752 | A | 5/1998 | Burkhart |
| 5,769,862 | A | 6/1998 | Kammerer et al. |
| 5,797,928 | A | 8/1998 | Kogasaka |
| 5,824,065 | A | 10/1998 | Gross |
| 5,931,868 | A | 8/1999 | Gross |
| 5,957,936 | A | 9/1999 | Yoon et al. |
| 5,971,447 | A | 10/1999 | Steck, III |
| 6,010,531 | A | 1/2000 | Donlon et al. |
| 6,074,417 | A | 6/2000 | Peredo |
| 6,269,819 | B1 | 8/2001 | Oz et al. |
| 6,332,893 | B1 | 12/2001 | Mortier et al. |
| 6,562,051 | B1 | 5/2003 | Bolduc et al. |
| 6,626,930 | B1 | 9/2003 | Allen et al. |
| 6,629,534 | B1 | 10/2003 | St. Goar et al. |
| 6,752,810 | B1 | 6/2004 | Gao et al. |
| 6,840,246 | B2 | 1/2005 | Downing |
| 6,921,408 | B2 | 7/2005 | Sauer |
| 6,940,246 | B2 | 9/2005 | Mochizuki et al. |
| 6,978,176 | B2 | 12/2005 | Lattouf |
| 6,991,635 | B2 | 1/2006 | Takamoto et al. |
| 6,997,950 | B2 | 2/2006 | Chawla |
| 7,112,207 | B2 | 9/2006 | Allen et al. |
| 7,291,168 | B2 | 11/2007 | Macoviak et al. |
| 7,294,148 | B2 | 11/2007 | McCarthy |
| 7,309,086 | B2 | 12/2007 | Carrier |
| 7,316,706 | B2 | 1/2008 | Bloom et al. |
| 7,373,207 | B2 | 5/2008 | Lattouf |
| 7,431,692 | B2 | 10/2008 | Zollinger et al. |
| 7,513,908 | B2 | 4/2009 | Lattouf |
| 7,534,260 | B2 | 5/2009 | Lattouf |
| 7,608,091 | B2 | 10/2009 | Goldfarb et al. |
| 7,618,449 | B2 | 11/2009 | Tremulis et al. |
| 7,632,308 | B2 | 12/2009 | Loulmet |
| 7,635,386 | B1 | 12/2009 | Gammie |
| 7,666,196 | B1 | 2/2010 | Miles |
| 7,744,609 | B2 | 6/2010 | Allen et al. |
| 7,837,727 | B2 | 11/2010 | Goetz et al. |
| 7,871,368 | B2 | 1/2011 | Zollinger et al. |
| 7,871,433 | B2 | 1/2011 | Lattouf |
| 7,959,650 | B2 | 6/2011 | Kaiser et al. |
| 8,029,518 | B2 | 10/2011 | Goldfarb et al. |
| 8,029,565 | B2 | 10/2011 | Lattouf |
| 8,043,368 | B2 | 10/2011 | Crabtree |
| 8,147,542 | B2 | 4/2012 | Maisano et al. |
| 8,187,323 | B2 | 5/2012 | Mortier et al. |
| 8,226,711 | B2 | 7/2012 | Mortier et al. |
| 8,241,304 | B2 | 8/2012 | Bachman |
| 8,252,050 | B2 | 8/2012 | Maisano et al. |
| 8,292,884 | B2 | 10/2012 | Levine et al. |
| 8,303,622 | B2 | 11/2012 | Alkhatib |
| 8,333,788 | B2 | 12/2012 | Maiorino |
| 8,382,829 | B1 | 2/2013 | Call et al. |
| 8,439,969 | B2 | 5/2013 | Gillinov et al. |
| 8,454,656 | B2 | 6/2013 | Tuval |
| 8,465,500 | B2 | 6/2013 | Speziali |
| 8,475,525 | B2 | 7/2013 | Maisano et al. |
| 8,500,800 | B2 | 8/2013 | Maisano et al. |
| 8,608,758 | B2 | 12/2013 | Singhatat et al. |
| 8,663,278 | B2 | 3/2014 | Mabuchi et al. |
| 8,771,296 | B2 | 7/2014 | Nobles et al. |
| 8,828,053 | B2 | 9/2014 | Sengun et al. |
| 8,852,213 | B2 | 10/2014 | Gammie et al. |
| 8,888,791 | B2 | 11/2014 | Jaramillo et al. |
| 8,940,008 | B2 | 1/2015 | Kunis |
| 9,131,884 | B2 | 9/2015 | Holmes et al. |
| 9,192,287 | B2 | 11/2015 | Saadat et al. |
| 10,076,414 | B2 | 9/2018 | Rourke et al. |
| 2002/0013571 | A1 | 1/2002 | Goldfarb et al. |
| 2003/0023254 | A1 | 1/2003 | Chiu |
| 2003/0094180 | A1 | 5/2003 | Benetti |
| 2003/0105519 | A1 | 6/2003 | Fasol et al. |
| 2003/0120264 | A1 | 6/2003 | Lattouf |
| 2003/0120341 | A1 | 6/2003 | Shennib et al. |
| 2004/0044365 | A1 | 3/2004 | Bachman |
| 2004/0093023 | A1 | 5/2004 | Allen et al. |
| 2004/0199183 | A1 | 10/2004 | Oz et al. |
| 2005/0004667 | A1 | 1/2005 | Swinford et al. |
| 2005/0019735 | A1 | 1/2005 | Demas |
| 2005/0075654 | A1 | 4/2005 | Kelleher |
| 2005/0119735 | A1 | 6/2005 | Spence et al. |
| 2005/0149067 | A1 | 7/2005 | Takemoto et al. |
| 2005/0149093 | A1 | 7/2005 | Pokorney |
| 2005/0154402 | A1 | 7/2005 | Sauer et al. |
| 2005/0216036 | A1 | 9/2005 | Nakao |
| 2005/0216077 | A1 | 9/2005 | Mathis et al. |
| 2005/0261710 | A1 | 11/2005 | Sakamoto et al. |
| 2005/0267493 | A1 | 12/2005 | Schreck et al. |
| 2006/0030866 | A1 | 2/2006 | Schreck |
| 2006/0100698 | A1 | 5/2006 | Lattouf |
| 2006/0111739 | A1 | 5/2006 | Staufer et al. |
| 2006/0167541 | A1 | 7/2006 | Lattouf |
| 2006/0190030 | A1 | 8/2006 | To et al. |
| 2006/0282088 | A1 | 12/2006 | Ryan |
| 2007/0001857 | A1 | 1/2007 | Hartmann et al. |
| 2007/0049952 | A1 | 3/2007 | Weiss |
| 2007/0055292 | A1 | 3/2007 | Ortiz et al. |
| 2007/0112422 | A1 | 5/2007 | Dehdashtian |
| 2007/0112425 | A1 | 5/2007 | Schaller et al. |
| 2007/0118151 | A1 | 5/2007 | Davidson |
| 2007/0118154 | A1 | 5/2007 | Crabtree |
| 2007/0149995 | A1 | 6/2007 | Quinn et al. |
| 2007/0197858 | A1 | 8/2007 | Goldfarb et al. |
| 2007/0213582 | A1 | 9/2007 | Zollinger et al. |
| 2007/0270793 | A1 | 11/2007 | Lattouf |
| 2008/0004597 | A1 | 1/2008 | Lattouf et al. |
| 2008/0009888 | A1 | 1/2008 | Ewers et al. |
| 2008/0065203 | A1 | 3/2008 | Khalapyan |
| 2008/0140093 | A1 | 6/2008 | Stone et al. |
| 2008/0167714 | A1 | 7/2008 | St. Goar et al. |
| 2008/0188893 | A1 | 8/2008 | Selvitelli et al. |
| 2008/0195126 | A1 | 8/2008 | Solem |
| 2008/0228223 | A1 | 9/2008 | Alkhatib |
| 2008/0249504 | A1 | 10/2008 | Lattouf et al. |
| 2008/0269781 | A1 | 10/2008 | Funamura et al. |
| 2009/0005863 | A1 | 1/2009 | Goetz et al. |
| 2009/0043153 | A1 | 2/2009 | Zollinger et al. |

(56) References Cited

U.S. PATENT DOCUMENTS

| | | | | |
|---|---|---|---|---|
| 2009/0105729 | A1 | 4/2009 | Zentgraf | |
| 2009/0105751 | A1 | 4/2009 | Zentgraf | |
| 2009/0276038 | A1 | 11/2009 | Tremulis et al. | |
| 2010/0023056 | A1* | 1/2010 | Johansson | A61B 17/0401 606/232 |
| 2010/0023117 | A1 | 1/2010 | Yoganathan et al. | |
| 2010/0023118 | A1 | 1/2010 | Medlock et al. | |
| 2010/0042147 | A1 | 2/2010 | Janovsky et al. | |
| 2010/0174297 | A1 | 7/2010 | Speziali | |
| 2010/0179574 | A1 | 7/2010 | Longoria et al. | |
| 2010/0210899 | A1 | 8/2010 | Schankereli | |
| 2010/0298930 | A1 | 11/2010 | Orlov | |
| 2011/0015476 | A1 | 1/2011 | Franco | |
| 2011/0022083 | A1 | 1/2011 | DiMatteo et al. | |
| 2011/0022084 | A1 | 1/2011 | Sengun et al. | |
| 2011/0028995 | A1 | 2/2011 | Miraki et al. | |
| 2011/0029071 | A1 | 2/2011 | Zlotnick et al. | |
| 2011/0060407 | A1 | 3/2011 | Ketai et al. | |
| 2011/0106106 | A1 | 5/2011 | Meier et al. | |
| 2011/0144743 | A1 | 6/2011 | Lattouf | |
| 2011/0264208 | A1 | 10/2011 | Duffy et al. | |
| 2011/0270278 | A1 | 11/2011 | Overes et al. | |
| 2011/0288637 | A1 | 11/2011 | De Marchena | |
| 2011/0307055 | A1 | 12/2011 | Goldfarb et al. | |
| 2012/0004669 | A1 | 1/2012 | Overes et al. | |
| 2012/0143215 | A1 | 6/2012 | Corrao et al. | |
| 2012/0150223 | A1 | 6/2012 | Manos et al. | |
| 2012/0179184 | A1 | 7/2012 | Orlov | |
| 2012/0184971 | A1 | 7/2012 | Zentgraf et al. | |
| 2012/0203072 | A1 | 8/2012 | Lattouf et al. | |
| 2012/0226294 | A1 | 9/2012 | Tuval | |
| 2012/0226349 | A1 | 9/2012 | Tuval et al. | |
| 2013/0018459 | A1 | 1/2013 | Maisano et al. | |
| 2013/0035757 | A1 | 2/2013 | Zentgraf et al. | |
| 2013/0253641 | A1 | 9/2013 | Lattouf | |
| 2013/0282059 | A1 | 10/2013 | Ketai et al. | |
| 2013/0345749 | A1 | 12/2013 | Sullivan et al. | |
| 2014/0031926 | A1 | 1/2014 | Kudlik et al. | |
| 2014/0039607 | A1 | 2/2014 | Kovach | |
| 2014/0067052 | A1 | 3/2014 | Chau et al. | |
| 2014/0114404 | A1 | 4/2014 | Gammie et al. | |
| 2014/0214152 | A1 | 7/2014 | Bielefeld | |
| 2014/0243968 | A1 | 8/2014 | Padala | |
| 2014/0364938 | A1 | 12/2014 | Longoria et al. | |
| 2015/0032127 | A1 | 1/2015 | Gammie et al. | |
| 2015/0045879 | A1 | 2/2015 | Longoria et al. | |
| 2018/0036126 | A1* | 2/2018 | Bobo, Jr. | A61F 2/2487 |
| 2019/0175346 | A1 | 6/2019 | Schaffner et al. | |
| 2020/0155315 | A1 | 5/2020 | Zhang et al. | |
| 2025/0134664 | A1* | 5/2025 | Medema | A61F 2/2457 |

FOREIGN PATENT DOCUMENTS

| | | | |
|---|---|---|---|
| GB | 944215 | A | 12/1963 |
| JP | 2013517110 | A | 5/2013 |
| WO | 2004037463 | A1 | 5/2004 |
| WO | 2006127509 | A2 | 11/2006 |
| WO | 2007100268 | A2 | 9/2007 |
| WO | 2007119057 | A1 | 10/2007 |
| WO | 2008013869 | A2 | 1/2008 |
| WO | 2008124110 | A3 | 12/2008 |
| WO | 2008143740 | A3 | 2/2009 |
| WO | 2006078694 | A3 | 4/2009 |
| WO | 2009081396 | A2 | 7/2009 |
| WO | 2010070649 | A1 | 6/2010 |
| WO | 2010105046 | A1 | 9/2010 |
| WO | 2011097355 | A2 | 8/2011 |
| WO | 2012137208 | A1 | 10/2012 |
| WO | 2013003228 | A1 | 1/2013 |
| WO | 2014093861 | A1 | 6/2014 |
| WO | 2015020816 | A1 | 2/2015 |
| WO | 2016192481 | A1 | 12/2016 |
| WO | 2017079153 | A1 | 5/2017 |
| WO | 2019126518 | A1 | 6/2019 |

OTHER PUBLICATIONS

Barbero-Marcial, M. et al., "Transxiphoid Approach Without Median Sternotomy for the Repair of Atrial Septa! Defects," (1998) Ann. Thorne. Surg., 65(3):771-774.

Braunberger, E. et al., "Very long-term results (more than 20 years) of valve repair with Carpentier's echniques in nonheumatic mitral valve insufficiency," (2001) Circulation, I 04:1-8-1-11.

Carpentier, Alain, "Cardiac valve surgery—the 'French coffection'," The Journal of Thoracic and Cardiovascular Surgery, vol. 86, No. 3, Sep. 1983, 15 pages.

David, T. E. et al., "Mitra! valve repair by replacement of chordae tendineae with polytetrafluoroethylene sutures," ( 1991) J. Thorne. Cardiovasc. Surg., 101 (3 ):495-50 I.

David, T. E. et al., "Replacement of chordae tendineae with Gore-Tex sutures: a ten-year experience," ( 1996) J. Heart Valve Dis., 5( 4 ):352-355.

Doty, D. B. et al., "Full-Spectrum Cardiac Surgery Through a Minimal Incision: Mini-Sternotomy (Lower Half) Technique," ( 1998) Ann. Thorne. Surg., 65(2):573-577.

Duran, C. M. G. et al., "Techniques for ensuring the correct length of new rnitral chords," (2003) .I. Heart Valve Dis., 12(2):156-161.

Eishi, K. et al., "Long-term results of artificial chordae implantation in patients with mitral valve prolapse," (1997) J. Heall Valve Dis., 6(6):594-598.

Frater, R. W. M. ct al., "Chordal replacement in mitral valve repair," ( 1990) Circulation, 82(suppl. IV):IV-125-IV-130.

Frater, R. W. M., "Anatomical rules for the plastic repair of a diseased mitral valve," ( 1964) Thorax. 19:458-464.

Huber, C.H. et al., "Direct Access Valve Replacement (DAVR)—are we entering a new era in cardiac surgery?" (2006) European Journal ofCardio-thoracic Surgery, 29:380-385.

Hvass, U. et al., "Papillary Muscle Sling: A New Functional Approach to Mitra! Repair in Patients With Ischernic Left Ventricular Dysfunction and Functional Mitral Regurgitation," (2003) Ann. Thorne. Surg., 75:809-811.

Kasegawa, H. ct al., "Simple method for detenning proper length of allificial chordae in mitral valve repair," ( 1994) Ann. Thorne. Surg., 57(1 ):237-239.

Kobayashi, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluorocthylcnc suture: a finite element study," (1996) J. Card. Surg., 11(2):136-145.

Langer, F. et al., "RING plus STRING: Papillary muscle repositioning as an adjunctive repair technique for ischemic mitral regurgitation," (2007) J. Thorne. Cardiovasc. Surg., 133( I): 247-249.

Maisano, F. et al., "The double-orifice technique as a standardized approach to treat mitral regurgitation due to severe rnyxomatous disease: surgical technique," (2000) European Journal of Cardio-thorncic Surgery, 17(3):201-205.

Merendino, K. A. et al., "The open con-ection of rheumatic mitral regurgitation and/or stenosis with special reference to regurgitation treated by posterornedial annuloplasty utilizing a pump-oxygenator," (1959) Annals of Surgery, 150(1 ):5-22.

Minatoya, K. et al., "Pathologic aspects of polytetrafluoroethylene sutures in human heart," ( 1996) Ann. Thorac. Surg., 61 (3 ):883-887.

Mohty, D. ct al., "Very long-term survival and durability ofmitral valve repair for mitral valve prolapse," (2001) Circulation, 104:1-1-1-7.

*Neochord, Inc.* v. *University of Maryland, Bal tim ore*, Case No. JPR2016-00208, Decision on Institution of Inter Faries Review,37 CFR §42. I 08, Paper 6, Entered May 24, 2016, 28 pages.

*Neochord, Inc.* v. *University of Maryland, Baltimore*, Case No. IPR2016-00208, Declaration of Dr. Lishan Aklog, dated Nov. 17, 2015, 91 pages.

*Neochord, Inc.* v. *University of Maryland, Baltimore*, Case No. IPR2016-00208, Petition for inter ParlesReview of U.S. Pat. No. 7,635,386, dated Nov. 18, 2015, 65 pages.

(56) References Cited

OTHER PUBLICATIONS

Nigro, J. J. et al., "Neochordal repair of the posterior mitral leaflet," (2004) J. Thorne. Cardiovasc. Surg., 127 (2):440-447.
Phillips, M. R. et al., "Repair of anterior leaflet mitral valve prolapse: chordal replacement versus chordal shrntening," (2000) Ann. Thorac. Surg., 69(1 ):25-29.
Russo, M. J. ct al. •Transapical Approach for Mitra! Valve Repair during Insertion of a Left Ventricular Assist Device, Hindawi Publishing Corporation, The Scientific World Journal, V olumc 2013, Article ID 925310, [ online], Retrieved from the internet: <URL: http://dx.doi.org/J 0.1155/2013/92531 O> Apr. 11, 2013, 4 pages.
Sarsam, M.A. I., "Simplified technique for determining the length of artificial cl1ordae in milral valve repair," (2002) Ann. Thorac. Surg., 73(5): 1659-1660.
Savage, E. B. et al., Use of mitral valve repair: analysis of contemporary United States experience reported to the society of thoracic surgeons national cardiac database, . . . (2003) Ann. Thorne. Surg., 75:820-825.
Speziali, G. et al., "Co!l'ection of Mitra! Valve Regurgitation by Off-Pump, Transapical Placement of Artificial Chordae Tendinae, Results of the European TACT Trial," AATS 93rd Annual Meeting 2013, www.aats. org, 26 pages.
Suematsu, Y. et al., "Three-dimensional echo-guided beating heaii surgery without cardiopulmonary bypass: Atrial septa! defect closure in a swine model," (2005) J. Thorne. Cardiovasc. Surg., 130: 1348-1357.
Von Oppell, U. 0. et al., "Chordal replacement for both minimally invasive and conventional mitral valve surgery using prcrncasurcd Gore-Tex loops," (2000) Ann. Thorne. Surg., 70(6):2166-2168.
Zussa, C. et al., Artificial rnitral valve chordae: experimental and clinical experience;• ( 1990) Ann. Thorne. Surg., 50 (3):367-373.
Zussa, C. et al., "Seven-year experience with chordal replacement with expanded polytetrafluoroethylene in floppyrnitral valve," (1994)1. Thorac. Cardiovasc. Surg., 108(1):37-41.
Zussa, C. et al., "Surgical technique for artificial rnitral chordae implantation," ( 1991) Journal of Cardiac Surgery, 6 (4):432-438.
Zussa, C., "Artificial chordae," (1995) J. Heart Valve Dis., 4(2):S249-S256.

* cited by examiner

ARTIFICIAL CHORDAE

CROSS REFERENCE TO RELATED APPLICATIONS

This application is a continuation of International Patent Application No. PCT/US2022/036453, filed Jul. 8, 2022, which claims the benefit of U.S. Patent Application No. 63/223,721, filed Jul. 20, 2021, the entire disclosures all of which are incorporated by reference for all purposes.

BACKGROUND

Field

The present disclosure generally relates to the field of cardiac valve repairs, and more particularly to minimally invasive cardiac valve repair operations.

Description of Related Art

Cardiac valve abnormalities can contribute to various heart conditions, adversely affecting supply of oxygenated blood to the rest of the body. Insufficient supply of oxygen can produce any number of symptoms, adversely affecting quality of life. Cardiac valve repair procedures can be performed to treat the abnormalities and alleviate the symptoms.

SUMMARY

Described herein are methods and devices relating to providing an artificial chordae system configured to provide regenerated native tissue tethering for one or more leaflets of a heart valve so as to tether the leaflets to a ventricular wall.

In some implementations, an artificial chordae system can comprise a surgical pad configured to be externally positioned over an opening formed in a portion of a heart wall adjacent to a heart ventricle; and a tether comprising a cord and a tissue ingrowth promoting coating over at least a portion of the cord. The tether can comprise a distal portion configured to couple to a heart valve leaflet, the tether being dimensioned to extend from the heart valve leaflet through the heart ventricle to the opening in the heart wall, and through the opening in the heart wall, a proximal portion of the tether being configured to be coupled to the surgical pad. The tissue ingrowth promoting coating can be configured to promote native tissue growth over the cord to provide regenerated native tissue over the cord for coupling the heart valve leaflet to the heart wall.

In some examples, the surgical pad can be biodegradable. In some examples, the surgical pad can comprise decellularized animal tissue. In some examples, the surgical pad can comprise bovine tissue. In some examples, the surgical pad can comprise porcine tissue. In some examples, the surgical pad can comprise blood vessel tissue. In some examples, the surgical pad can be a sheet of the decellularized animal tissue.

In some examples, the surgical pad can comprise a second tissue ingrowth promoting coating over at least a portion of a decellularized animal tissue membrane. In some examples, at least a portion of the tether extending between the heart valve leaflet and the portion of the heart wall can comprise the tissue ingrowth promoting coating over the cord. In some examples, at least one of the tissue ingrowth promoting coating of the tether and the second tissue ingrowth promoting coating of the surgical pad can comprise a protein. In some examples, the protein can comprise an extracellular matrix (ECM) protein. The protein can comprise fibronectin. The protein can comprise laminin. The protein can comprise collagen. In some examples, the protein can comprise an insect protein. In some examples, the protein can comprise a spider protein. In some examples, the protein can comprise a synthetic animal protein.

In some examples, the cord can comprise a biomimetic micropattern on at least a portion thereof. The biomimetic micropattern can comprise a plurality of grooves.

In some examples, the cord can be non-biodegradable. The cord can be an expanded polytetrafluoroethylene (ePTFE) cord.

In some examples, the cord can be biodegradable. The cord can comprise a biodegradable polymer. In some examples, the cord can comprise a core portion and an outer layer portion surrounding the core portion, the core portion comprising a composition configured to have a degradation rate slower than that of the outer layer portion. In some examples, the cord can comprise a middle portion between a first end portion and a second end portion, the middle portion comprising a composition configured to have a degradation rate slower than that of the first and the second end portions.

In some examples, the distal portion of the tether can comprise an anchor configured to be positioned over a surface of the heart valve leaflet oriented away from the heart ventricle to couple the tether to the heart valve leaflet, the anchor comprising the tissue ingrowth promoting coating thereon. In some examples, the anchor can comprise a bulky-knot, the bulky-knot being formed using a portion of the tether.

In some implementations, a tether can comprise a cord; and a tissue ingrowth promoting coating over at least a portion of the cord, the tissue ingrowth promoting coating being configured to promote native tissue growth over the cord to provide regenerated native tissue over the cord for coupling a heart valve leaflet to a ventricular heart wall. The tether can comprise a distal portion configured to couple to the heart valve leaflet, and the tether being configured to extend proximally from the heart valve leaflet through a heart ventricle to a portion of the ventricular heart wall to couple the heart valve leaflet to the ventricular heart wall.

In some examples, the tissue ingrowth promoting coating can comprise an extracellular matrix (ECM) protein. In some examples, the tissue ingrowth promoting coating can comprise an insect protein. In some examples, the tissue ingrowth promoting coating can comprise a spider protein. In some examples, the tissue ingrowth promoting coating can comprise a synthetic animal protein.

In some examples, the cord can comprise a biomimetic micropattern on at least a portion thereof. In some examples, the cord can be an expanded polytetrafluoroethylene (ePTFE) cord. In some examples, the cord can comprise a biodegradable polymer.

In some implementations, a method of deploying an artificial chordae system can comprise coupling a distal portion of a tether to a heart valve leaflet, the tether comprising a tissue ingrowth promoting coating over at least a portion of a cord. The method can include extending the tether from the heart valve leaflet through a heart ventricle to a portion of a heart wall adjacent to the heart ventricle, the heart valve leaflet controlling blood flow into and out of the heart ventricle. The method can include extending the tether through an opening formed on the portion of the heart wall; and coupling a proximal portion of the tether to a surgical pad positioned over an externally oriented surface of the heart wall and the opening formed in the portion of the heart wall.

In some examples, the surgical pad can comprise decellularized animal tissue. In some examples, the surgical pad can comprise a second tissue ingrowth promoting coating on at least a portion thereof. In some examples, the cord can be biodegradable.

In some examples, at least one of the tissue ingrowth promoting coating of the tether and the second tissue ingrowth promoting coating of the surgical pad can comprise an extracellular matrix (ECM) protein.

In some examples, coupling the distal portion of the tether to the heart valve leaflet can comprise providing an anchor on an atrial facing surface of the heart valve leaflet.

In some examples, providing the anchor can comprise forming a bulky-knot anchor over the atrial facing surface of the heart valve leaflet using the tether.

Methods and structures disclosed herein for treating a patient also encompass analogous methods and structures performed on or placed on a simulated patient, which is useful, for example, for training; for demonstration; for procedure and/or device development; and the like. The simulated patient can be physical, virtual, or a combination of physical and virtual. A simulation can include a simulation of all or a portion of a patient, for example, an entire body, a portion of a body (e.g., thorax), a system (e.g., cardiovascular system), an organ (e.g., heart), or any combination thereof. Physical elements can be natural, including human or animal cadavers, or portions thereof; synthetic; or any combination of natural and synthetic. Virtual elements can be entirely in silica, or overlaid on one or more of the physical components. Virtual elements can be presented on any combination of screens, headsets, holographically, projected, loud speakers, headphones, pressure transducers, temperature transducers, or using any combination of suitable technologies.

For purposes of summarizing the disclosure, certain aspects, advantages and novel features have been described herein. It is to be understood that not necessarily all such advantages may be achieved in accordance with any particular instance. Thus, the disclosed instances may be carried out in a manner that achieves or optimizes one advantage or group of advantages as taught herein without necessarily achieving other advantages as may be taught or suggested herein.

BRIEF DESCRIPTION OF THE DRAWINGS

Various instances are depicted in the accompanying drawings for illustrative purposes and should in no way be interpreted as limiting the scope of the inventions. In addition, various features of different disclosed instances can be combined to form additional instances, which are part of this disclosure. Throughout the drawings, reference numbers may be reused to indicate correspondence between reference elements. However, it should be understood that the use of similar reference numbers in connection with multiple drawings does not necessarily imply similarity between respective instances associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some instances or configurations.

DETAILED DESCRIPTION

Figure 1:
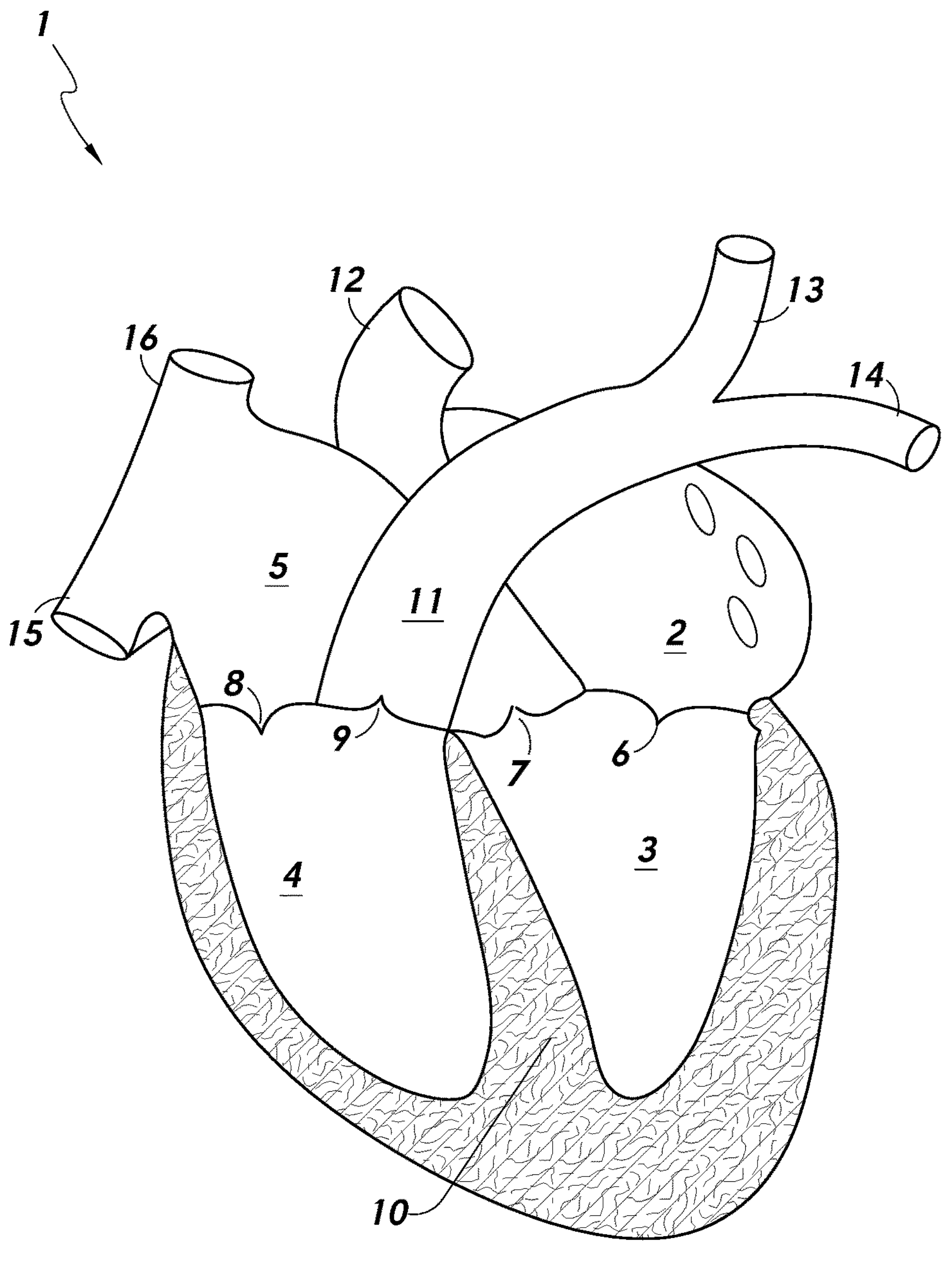
FIG. 1 is a cross-sectional view of a human heart.

The headings provided herein are for convenience only and do not necessarily affect the scope or meaning of the claimed invention.

The present disclosure relates to devices and methods for providing regenerated native tissue tethering to couple one or more leaflets of a heart valve to a ventricular portion of the heart wall.

Although certain preferred instances and examples are disclosed below, inventive subject matter extends beyond the specifically disclosed instances to other alternative instances and/or uses and to modifications and equivalents thereof. Thus, the scope of the claims that may arise herefrom is not limited by any of the particular instances described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain instances; however, the order of description should not be construed to imply that these operations are order dependent. Additionally, the structures, systems, and/or devices described herein may be embodied as integrated components or as separate components. For purposes of comparing various instances, certain aspects and advantages of these instances are described. Not necessarily all such aspects or advantages are achieved by any particular instance. Thus, for example, various instances may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred instances. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element (s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

FIG. 1 is a schematic diagram showing various features of a human heart 1. The heart 1 includes four chambers, namely the left atrium 2, the left ventricle 3, the right ventricle 4, and the right atrium 5. A wall of muscle, referred to as the septum 10, separates the left atrium 2 and right atrium 5, and the left ventricle 3 and right ventricle 4. Blood flow through the heart 1 is at least partially controlled by four valves, the mitral valve 6, aortic valve 7, tricuspid valve 8, and pulmonary valve 9. The mitral valve 6 separates the left atrium 2 and the left ventricle 3 and controls blood flow therebetween. The aortic valve 7 separates and controls blood flow between the left ventricle 3 and the aorta 12. The tricuspid valve 8 separates the right atrium 5 and the right ventricle 4 and controls blood flow therebetween. The pulmonary valve 9 separates the right ventricle 4 and the pulmonary trunk or artery 11, controlling blood flow therebetween.

In a healthy heart, the heart valves can properly open and close in response to a pressure gradient present during various stages of the cardiac cycle (e.g., relaxation and contraction) to at least partially control the flow of blood to a respective region of the heart and/or to blood vessels. Deoxygenated blood arriving from the rest of the body generally flows into the right side of the heart for transport to the lungs, and oxygenated blood from the lungs generally flows into the left side of the heart for transport to the rest of the body. During ventricular diastole, deoxygenated blood arrive in the right atrium 5 from the inferior vena cava 15 and superior vena cava 16 to flow into the right ventricle 4, and oxygenated blood arrive in the left atrium 2 from the pulmonary veins to flow into the left ventricle 3. During ventricular systole, deoxygenated blood from the right ventricle 4 can flow into the pulmonary trunk ii for transport to the lungs (e.g., via the left 14 and right 13 pulmonary arteries), and oxygenated blood can flow from the left ventricle 3 to the aorta 12 for transport to the rest of the body.

A number of conditions can contribute to a higher than normal pressure in the left atrium. Dysfunction of the mitral valve can contribute to elevated left atrial pressure. Conditions such as mitral valve regurgitation and/or stenosis may result in difficulty in pumping blood from the left atrium to the left ventricle, contributing to elevated pressure in the left atrium. Valve stenosis can cause a valve to become narrowed or obstructed. Mitral valve stenosis can restrict blood flow from the left atrium to the left ventricle. Valve regurgitation occurs when a valve does not close properly. For example, regurgitation can occur due to improper coaptation of the valve leaflets, such as due to prolapse of one or more of the valve leaflets. Mitral valve regurgitation can result in blood flow leakage back into the left atrium 2 from the left ventricle 3 when the left ventricle 3 contracts. Restricted flow of blood from the left atrium 2 into the left ventricle 3, and blood flow leakage from the left ventricle 3 back into the left atrium 2 can both contribute to elevated atrial pressure. Dysfunction in the left ventricle 3 can also contribute to elevated left atrial pressure. Elevated left atrial pressure may lead to left atrial enlargement, producing symptoms such as shortness of breath during exertion, fatigue, chest pain, fainting, abnormal heartbeat, and swelling of the legs and feet.

The disclosure herein provides one or more devices and methods related to providing an artificial chordae system configured to provide regenerated native tissue tethering for one or more leaflets of a heart valve. The artificial chordae system can comprise a tether which has a cord and a tissue ingrowth promoting coating over at least a portion of the cord. The tether can be configured to couple a heart valve leaflet to a ventricular heart wall. A distal portion of the tether can be configured to couple the heart valve leaflet and a proximal portion of the tether can be configured to be coupled to the ventricular heart wall. In some instances, the tether can have a cord extending therethrough and a tissue ingrowth promoting coating over the entire or substantially entire length of the cord.

The artificial chordae system can comprise a surgical pad. The surgical pad can be configured to be positioned externally of the heart over an opening formed in a portion of a heart wall adjacent to the heart ventricle. The tether can be dimensioned to extend from the heart valve leaflet through the heart ventricle to the opening in the heart wall, and through the opening in the heart wall, such that the proximal portion of the tether can be coupled to the surgical pad. The surgical pad can comprise a biodegradable membrane. For example, the surgical pad can comprise an antigen removal processed animal tissue membrane, including bovine tissue and/or porcine tissue. In some instances, the surgical pad can comprise a tissue ingrowth promoting coating. For example, the surgical pad can comprise a tissue ingrowth promoting coating over an antigen removal processed animal tissue membrane. In some instances, the surgical pad does not have a tissue ingrowth promoting coating. The surgical pad can be an antigen removal processed animal tissue membrane, including an antigen removal processed bovine tissue membrane or an antigen removal processed porcine tissue membrane.

The tissue ingrowth promoting coating can be configured to promote native tissue growth over the cord and/or the surgical pad. After deployment of the tether and surgical pad to their respective target sites, native tissue adjacent to the tether and/or surgical pad can migrate onto and grow on the tether and/or surgical pad. Growth of the native tissue over the tether and/or surgical pad can provide tethering for the heart valve leaflet comprising regenerated native tissue. The artificial chordae system described herein can be configured to provide regenerated native tissue to couple the heart valve leaflet to the ventricular wall for treating improper coaptation of the valve leaflets.

A heart valve repair procedure to improve or restore valve function can comprise deploying an artificial chordae system as described herein. The artificial chordae system can be delivered using a minimally invasive technique. In some instances, the delivery can be performed while the heart is beating. For example, the procedure to deliver the artificial chordae system can be a minimally invasive beating heart procedure. In some instances, mitral valve repair procedures can comprise deploying an artificial chordae system as described herein to alleviate mitral valve dysfunction, including mitral valve prolapse.

The methods, operations, steps, etc. described herein can be performed on a living animal or simulated on a human or animal cadaver, cadaver heart, simulator (e.g., with the body parts, tissue, etc. being simulated), etc. For example, methods for treating a patient include methods for simulating the treatment on a simulated patient or anthropogenic ghost, which can include any combination of physical and virtual elements. Examples of physical elements include human or animal cadavers; any portions thereof, including organ systems, whole organs, or tissue; and manufactured elements, which can simulate the appearance, texture, resistance, or other characteristic. Virtual elements can include visual elements provided on a screen, or projected on a surface or volume, including virtual reality and augmented reality implementations. Virtual elements can also simulate other sensory stimuli, including sound, feel, and/or odor.

It will be understood that one or more components of the systems described herein can undergo various processes in preparation for use in the procedures, including for example sterilization processes. One or more components of the systems can be sterilized. For example, surgical pads and/or tethers as described herein can be sterilized surgical pads and/or sterilized tethers.

The term “associated with” is used herein according to its broad and ordinary meaning. For example, where a first feature, element, component, device, or member is described as being “associated with” a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

Figure 2:
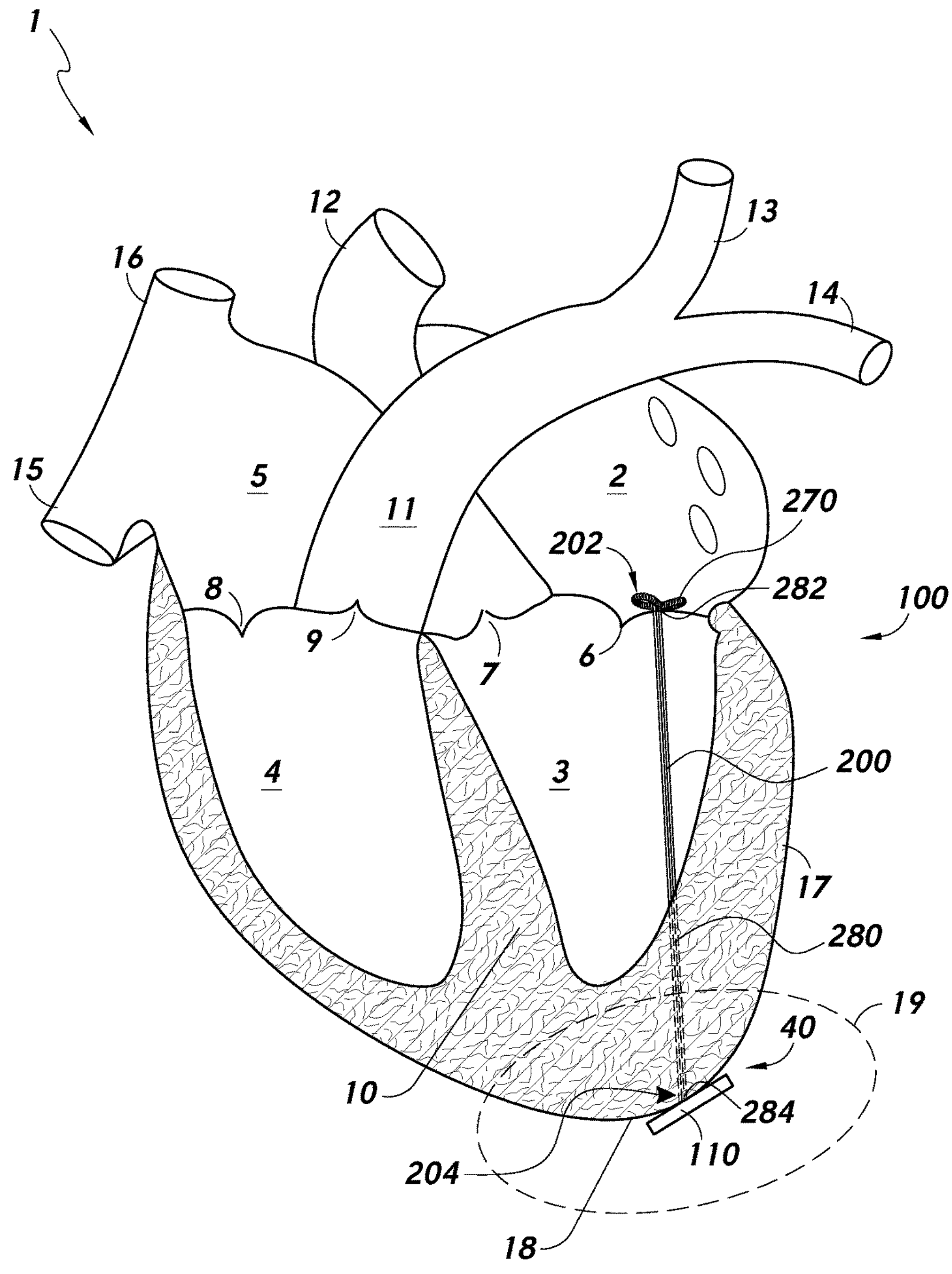
FIG. 2 is a cross-sectional view of the human heart and an artificial chordae system deployed into the human heart to couple a mitral valve leaflet of the heart to a ventricular wall of the heart, according to some instances.

FIG. 2 shows an artificial chordae system 100 deployed into the heart 1. The artificial chordae system 100 can comprise a surgical pad 110 and a tether 200 configured to couple a heart valve leaflet of the mitral valve 6 to the surgical pad no. The surgical pad no can be positioned over an externally oriented portion of the heart wall 17. A distal portion 202 of the tether 200 can be configured to be coupled to the heart valve leaflet. A proximal portion 204 of the tether 200 can be configured to be coupled to the surgical pad no. As described in further detail with reference to FIGS. 3 and 4, the tether 200 can comprise a cord and a tissue ingrowth promoting coating over at least a portion of the cord. The tether 200 can comprise a cord extending through an entire or substantially entire length thereof and a tissue ingrowth promoting coating over an entire or substantially entire length of the cord. The surgical pad 110 can comprise a biodegradable membrane, for example a biodegradable membrane comprising animal tissue, including an antigen removal processed animal tissue. In some instances, the surgical pad no can optionally comprise a tissue ingrowth promoting coating. In some instances, the surgical pad 110 does not have a tissue ingrowth promoting coating. The tissue ingrowth promoting coating can be over one or more surfaces of the biodegradable membrane. The tissue ingrowth promoting coating of the tether 200 and the tissue ingrowth promoting coating of the surgical pad 110 may or may not have the same composition. The respective tissue ingrowth promoting coating can be configured to promote migration onto and growth of native tissue over the cord of the tether 200 and the membrane of the surgical pad no. The tissue ingrowth promoting coatings can encourage migration of native heart tissue onto the tether 200 or surgical pad 110 and growth of the native heart tissue on the tether 200 or surgical pad no.

The artificial chordae system 100 can facilitate regeneration of tethering for the heart valve leaflet using native heart tissue. Native tissue adjacent to the tether 200 and the surgical pad no can migrate onto and grow on the tether 200 and surgical pad no, respectively. Native tissue can migrate onto and grow on the tether 200 and surgical pad 110 to provide tethering comprising regenerated tissue for the heart valve leaflet to the heart wall 17. At least a portion of each of the tether 200 and surgical pad 110 may be biodegradable. For example, at least a part of each of the tether 200 and surgical pad 110 can degrade and/or be consumed as the native tissue grows over the tether 200 and surgical pad no. In some instances, the tether 200 can be completely or substantially completely biodegradable. For example, both the cord and the tissue ingrowth promoting coating can be biodegradable. As the native tissue grows over the tether 200, the cord and the tissue ingrowth promoting coating can be consumed and/or degrade over time. Native tissue can completely replace the tether 200, and/or the tether 200 can be integrated as part of the newly formed native tissue tethering. A regenerated native tissue chordae can replace the tether 200 for coupling the heart valve leaflet to the heart wall 17. In some instances, the surgical pad no can be completely or substantially completely biodegradable. For example, the animal tissue membrane and the tissue ingrowth promoting coating can be biodegradable. As the native tissue grows over the surgical pad no, the animal tissue membrane and the tissue ingrowth promoting coating can be consumed and/or degrade over time such that native tissue completely replaces the surgical pad 110, and/or the surgical pad 110 can be integrated as part of newly formed native tissue. The artificial chordae system 100 can provide a regenerated native tissue tethering system that couples the heart valve leaflet to the heart wall 17. The tethering system can entirely or substantially entirely be regenerated native tissue. A tethering system that is entirely or substantially entirely of regenerated native tissue can provide desired mechanical strength while reducing or eliminating biocompatibility issues.

In some examples, at least a portion of the tether 200 can be non-biodegradable. For example, the cord may be non-biodegradable. The tissue ingrowth promoting coating can be consumed and/or degrade over time as native heart tissue migrates onto and grow on the cord, while the cord remains coupled to the heart valve leaflet and the heart wall. The remaining cord can provide additional strength for the coupling between the heart valve leaflet and the heart wall.

As shown in FIG. 2, in the deployed state, the tether 200 can extend from the heart valve leaflet through an adjacent heart ventricle to the heart wall 17. The heart valve leaflet controls blood flow into and out of the heart ventricle. The distal portion 202 of the tether 200 can be coupled to the heart valve leaflet. In the deployed state, the distal portion 202 of the tether 200 can comprise an anchor 270. The anchor 270 can be configured to be positioned over a surface of the heart valve leaflet oriented away from the heart ventricle, such as an atrium-facing surface of the leaflet. The tether 200 can comprise the anchor 270 and an elongate portion 280. For example, a distal portion 282 of the elongate portion 280 can be associated with the anchor 270. The anchor 270 can be coupled to the distal portion 282 of the elongate portion 280. A proximal portion 284 of the elongate portion 280 can be configured to be associated with the surgical pad no. For example, the proximal portion 284 can be coupled to the surgical pad no. The anchor 270 can comprise any number of anchoring mechanisms configured to facilitate maintaining the tether 200 anchored to the leaflet. As described in further detail herein, in some instances, the anchor 270 can comprise a suture-style knot, including a bulky knot. The elongate portion 280 can comprise one or more tether tails. For example, the elongate portion 280 can comprise two tether tails 280*a*, 280*b* (not shown). The anchor 270 can be associated with a distal portion of the tether tails 280*a*, 280*b*. A proximal portion of the tether tails 280*a*, 280*b* can be coupled to the surgical pad no.

In some instances, the anchor 270 can be a knot formed using the same material as the elongate portion 280. In some instances, the elongate portion 280 and the anchor 270 can be an integral piece. In some instances, the elongate portion 280 and the anchor 270 can be formed using a single tether. For example, the tether tails and the anchor 270 can be formed using an integral piece of tether, where the tether comprises a cord extending through an entire or substantially entire length thereof and a tissue ingrowth promoting coating over an entire or substantially entire length of the cord. The tether can comprise a respective portion configured to form the anchor 270 and a respective portion configured to form the elongate portion 280. For example, the anchor 270 and the elongate portion 280 can be formed using a unitary piece of tether such that while the tether is in the deployed state, a respective portion of the tether forms the anchor 270, and a respective portion of the tether forms the elongate portion 280.

As described in further detail herein, in some cases, a transapical approach can be used to gain access into the heart 1 to deploy the tether 200. The heart wall 17 can be punctured in the apical region 19 to form an opening so as to allow delivery of the tether 200 into a heart ventricle, such as to couple the distal portion 202 of the tether 200 to a heart valve leaflet which facilitates control blood flow into and out of the heart ventricle. The apical region 19 is schematically shown in FIG. 1 as the area within the dashed circle. As used herein, the "apical region" can include the inferior tip of the heart 1. The inferior tip is referred to herein as the apex 18 of the heart 1 and is generally located on the midclavicular line, in the fifth intercostal space. The apex 18 can be considered part of the greater apical region 19. Generally, the apical region 19 of the heart is a bottom region of the heart that is within the left or right ventricular region but is distal to the mitral 6 and tricuspid 8 valves and toward the tip of the heart 1. More specifically, the apical region 19 may be considered to be within about 20 centimeters (cm) to the right or to the left of the median axis of the heart 1. The opening can be formed on a portion of the heart wall 17 in the apical region 19 adjacent to the heart ventricle. The tether 200 can be dimensioned to extend from the heart valve leaflet through the heart ventricle, and to the opening in the heart wall 17. The tether 200 can extend through the opening in the heart wall 17 so as to couple the proximal portion 204 of the tether 200 to the surgical pad no positioned externally over the opening, tethering the heart valve leaflet to the heart wall 17.

FIG. 2 shows the artificial chordae system 100 deployed to couple a mitral valve leaflet to the heart wall 17. The artificial chordae system 100 can be deployed to reduce the degree of mitral regurgitation in patients suffering from mitral regurgitation caused by, for example, midsegment prolapse of valve leaflets as a result of degenerative mitral valve disease. Mitral valve repair surgeries can comprise accessing the mitral valve 6 from within the left ventricle 3, where entry into the left ventricle 3 can be achieved through an opening 40 formed in the apical region 19 of the heart 1. The artificial chordae system 100 can be deployed through the opening 40 to couple the mitral valve leaflet to the left ventricular heart wall. Coupling the leaflet to the heart wall 17 can facilitate reshaping of the mitral valve 6, such as to reduce or eliminate leaflet prolapse. The artificial chordae system 100 can serve to improve coaptation of the leaflet. In some instances, the artificial chordae system 100 can comprise more than one tether 200 for coupling the heart valve leaflet to the heart wall 17. It will be understood that an artificial chordae system can be used to provide tethering for one or more leaflets of a valve other than the mitral valve, such as the tricuspid valve.

The heart wall 17 can be punctured in the apical region 19 of the heart wall 17 adjacent to the left ventricle 3 to form the opening 40 so as to allow delivery of the tether 200 to the mitral valve 6. The distal portion 202 of the tether 200 can be coupled to a leaflet of the mitral valve 6. The tether 200 can be dimensioned to extend from the leaflet of the mitral valve 6 through the left ventricle 3 to the heart wall 17, such as to the opening 40 formed in the heart wall 17. The tether 200 can extend through the opening 40. The proximal portion 204 of the tether 200 can be coupled to the surgical pad no positioned externally over the opening 40. The distal portion 202 of the tether 200 can be delivered to an atrial facing surface of the mitral valve leaflet. For example, the mitral valve leaflet can be punctured such that the anchor 270 can be positioned at least partially over an upper surface of the leaflet. The anchor 270 can be positioned over the atrial facing surface of the mitral valve leaflet, such as a surface of the leaflet facing the left atrium. The elongate portion 280 of the tether 200 can extend proximally from the anchor 270. The elongate portion 280 of the tether 200 can be dimensioned to extend from the leaflet of the mitral valve 6 through the left ventricle 3 to the opening 40 in the heart wall 17, and through the opening 40 in the wall 17 to couple to the surgical pad no. For example, the two tether tails 280*a*, 280*b* can extend from the anchor 270, through the leaflet and the left ventricle 3 to the opening 40, and through the opening 40 to couple to the surgical pad no. The surgical pad no can be positioned over the opening 40 formed in the heart wall 17 and/or over a portion of the heart wall 17 adjacent to the left ventricle 3. In some instances, the surgical pad no can be positioned over a pericardium layer of the heart 1.

Figure 3:
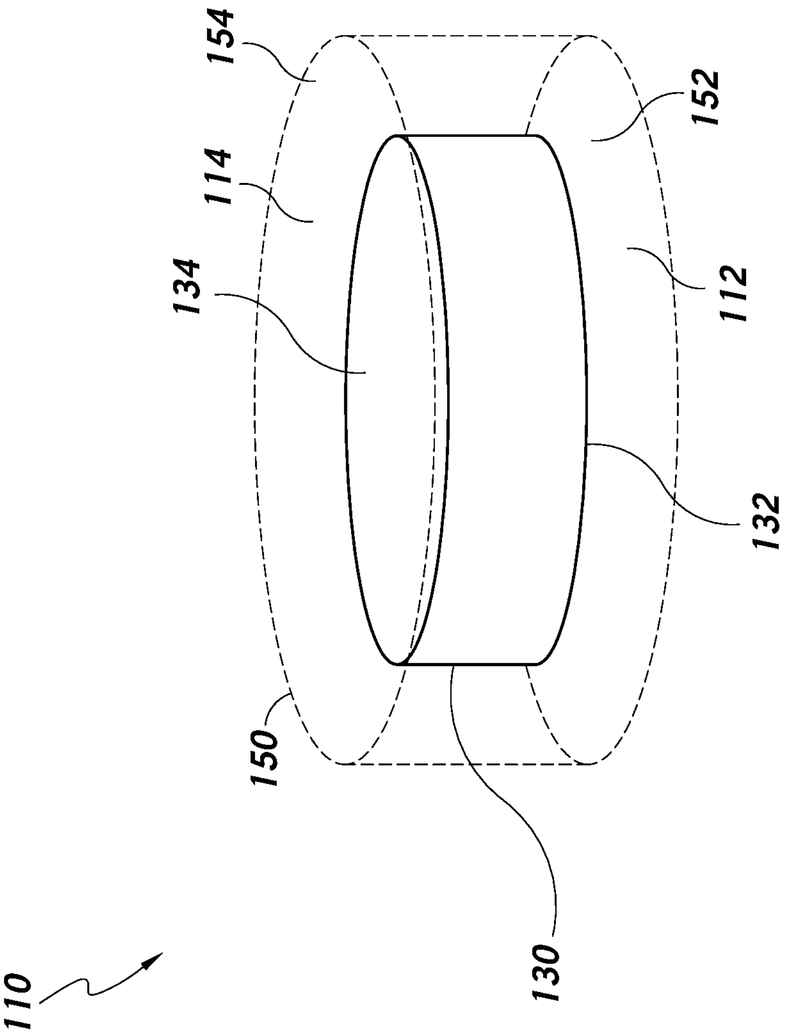
FIG. 3 is a perspective view of the surgical pad of the artificial chordae system described with reference to FIG. 2.

FIG. 3 shows the surgical pad no described with reference to FIG. 2. As described herein, native heart tissue cells can migrate onto and grow on the surgical pad no. In some instances, the surgical pad no can be biodegradable. The surgical pad no can degrade, be consumed by the native tissue, and/or be integrated as part of the heart wall, as native heart tissue grows over the surgical pad no. The surgical pad no can be configured to promote migration of adjacent native tissue cells onto the surgical pad no. In some instances, native tissue cells which has migrated onto the surgical pad 110 can produce extracellular matrix (ECM), thereby encouraging growth of the native tissue cells on the surgical pad 110. The extracellular matrix (ECM) and/or the native tissue cells can progressively replace the surgical pad no.

As described herein, the surgical pad no can be positioned externally of the heart. The surgical pad no can be configured to be positioned over an opening formed in a ventricular heart wall and/or a portion of the heart wall adjacent to the opening, such that a first surface 112 of the surgical pad no is oriented toward the heart and a second surface 114 is oriented away from the heart. The second surface 114 can have an opposing orientation relative to the first surface 112. The surgical pad 110 can be configured to be coupled to one or more tethers as described herein. In some instances, the one or more tethers can extend through surgical pad no to be secured to the surgical pad no. For example, the one or more tethers can extend through the opening in the heart wall, and extend from the first surface 112 through the surgical pad 110 to the second surface 114 of the surgical pad 110. In some instances, the one or more tethers can form one or more knots over the second surface 114 to secure the tethers to the surgical pad no.

The surgical pad no can comprise a biodegradable membrane 130. In some examples, the surgical pad no is the biodegradable membrane 130. For example, a first surface 132 of the biodegradable membrane 130 can be positioned over and/or on and in contact with an externally oriented surface of the heart and a second opposing surface 134 of the biodegradable membrane 130 can be oriented away from the heart. The biodegradable membrane 130 can comprise a material configured to facilitate migration of native tissue onto and/or growth of native tissue on the biodegradable membrane 130 such that native tissue can replace the biodegradable membrane 130.

The biodegradable membrane 130 can comprise an animal tissue, including an animal tissue which has undergone an antigen removal process, such as a sheet of antigen removal processed animal tissue. The biodegradable membrane 130 can comprise any one of a number of animal tissues which can undergo an antigen removal process, including one or more of bovine tissue, porcine tissue, and/or blood vessel tissue which has undergone an antigen removal process. The biodegradable membrane 130 can be an antigen removal processed bovine tissue, porcine tissue, or blood vessel tissue. For example, the biodegradable membrane 130 can be a sheet of bovine tissue, porcine tissue, or blood vessel tissue which has undergone antigen removal process. In some instances, the biodegradable membrane 130 can comprise a decellularized tissue membrane. For example, the biodegradable membrane 130 can be a decellularized bovine tissue, porcine tissue, or blood vessel tissue. The biodegradable membrane 130 can be a sheet of decellularized bovine tissue, porcine tissue, or blood vessel tissue. One or more tethers as described herein can be threaded through the sheet of antigen removal processed tissue to secure the tethers to the heart wall.

In some examples, the surgical pad no can optionally include a tissue ingrowth promoting coating 150. The surgical pad 110 can comprise the biodegradable membrane 130 and the tissue ingrowth promoting coating 150 over one or more surfaces of the biodegradable membrane 130. FIG. 3 shows the tissue ingrowth promoting coating 150 over all surfaces of the biodegradable membrane 130. For example, a first portion 152 of the tissue ingrowth promoting coating 150 over the first surface 132 of the biodegradable membrane 130 can be configured to be over and/or on and in contact with the heart wall, and a second portion 154 of the tissue ingrowth promoting coating 150 over the second surface 134 of the biodegradable membrane 130 can be configured to be oriented away from the heart wall. However, it will be understood that the tissue ingrowth promoting coating 150 can be over fewer surfaces. In some instances, the tissue ingrowth promoting coating 150 can be over only a first surface 132 and/or second surface 134 of the biodegradable membrane 130. As described in further detail herein, the tissue ingrowth promoting coating 150 can comprise one or more components configured to promote growth of native tissue.

Surgical pads as described herein can have a number of different shapes. Although the surgical pad no is shown in FIG. 3 as having a rounded shape, such as a circular shape, it will be understood that a variety of other shapes can be applicable. In some instances, a surgical pad can have a rectangular shape.

Figure 4:
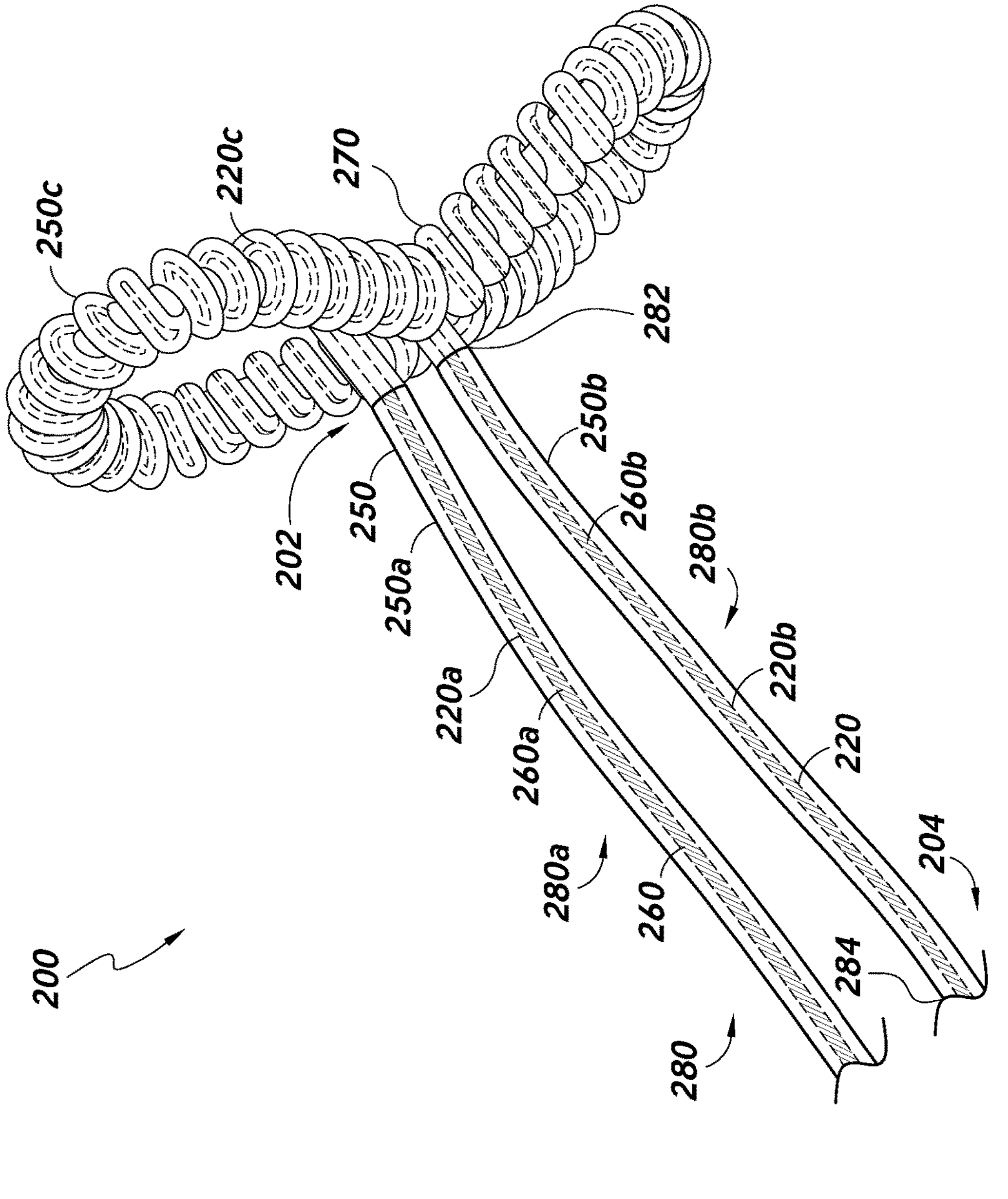
FIG. 4 is a perspective view of the tether of the artificial chordae system described with reference to FIG. 2.

FIG. 4 shows the tether 200 of the artificial chordae system 100 described with reference to FIG. 2 in further detail. The tether 200 is shown in the deployed state, where the distal portion 202 of tether 200 can be configured to be coupled to the heart valve leaflet and the proximal portion 204 of the tether 200 can be configured to be coupled to a heart wall. The tether 200 can comprise a cord 220 and a tissue ingrowth promoting coating 250 over at least a portion of the cord 220. The coating 250 can be over the entirety or substantially entirety of the cord 220. The coating 250 can be on an externally oriented surface of the cord 220. For example, the coating 250 can be around and in contact with the cord 220 along an entire or substantially entire length of the cord 220. In the deployed state, the distal portion 202 of the tether 200 can comprise the anchor 270. The elongate portion 280 can extend proximally from the anchor 270. The elongate portion 280 can comprise a distal portion 282 coupled to the anchor 270 and a proximal portion 284 configured to be coupled to the heart wall.

The elongate portion 280 can comprise two tether tails 280*a*, 280*b*. The anchor 270 and/or the tether tails 280*a*, 280*b* can comprise respective portions of the cord 220 and the tissue ingrowth promoting coating 250 over the respective portions of the cord 220. In some instances, at least a portion of the elongate portion 280, such as the tether tails 280*a*, 280*b*, can comprise the tissue ingrowth promoting coating 250 over the cord 220. In some instances, at least a portion of the elongate portion 280, such as the tether tails 280*a*, 280*b*, extending between the heart valve leaflet and the heart wall can comprise the tissue ingrowth promoting coating 250 over the cord 220. In some instances, the tissue ingrowth promoting coating 250 can be on the entirety or substantially entirety of the cord portions 220*a*, 220*b* of the elongate portion 280. For example, the tether tails 280*a*, 280*b* can comprise respective tissue ingrowth promoting coating portions 250*a*, 250*b* over the cord portions 220*a*, 220*b*. Alternatively, the tissue ingrowth promoting coating 250 can be on less than the entirety of the cord portions 220*a*, 220*b* of the elongate portion 280. In some instances, the ingrowth promoting coating 250 can be on only portions of the cord portions 220*a*, 220*b* configured to be within the heart, including portions of the cord portions 220*a*, 220*b* configured to be between the heart valve leaflet and the heart wall. In some examples, the tissue ingrowth promoting coating 250 can be on the anchor 270, including an entirety or substantially entirety of the anchor 270. For example, the anchor 270 can comprise a cord portion 220C extending therethrough and a tissue ingrowth promoting coating 250*c* over the cord portion 220C.

In some instances, the tissue ingrowth promoting coating 250 can be over all or substantially all externally oriented surfaces of the cord 220 along an entire or substantially entire length of the cord 220. In some instances, the tether 200 can comprise the cord 220 extending therethrough and the tissue ingrowth promoting coating 250 can be over an entire or substantially entire length of the cord 220. As described herein, the anchor 270 can comprise a suture-knot-style anchor. For example, the anchor 270 can be a bulky-knot. The bulky-knot can be formed using a portion of the tether 200. In some examples, both the anchor 270 and the elongate portion 280, including the tether tails 280*a*, 280*b*, can be formed using one tether. The anchor 270 and the elongate portion 280 can be a unitary piece. For example, the cord 220 can extend through an entire or substantially entire length of the tether 200 and the tissue ingrowth promoting coating 250 can be over an entire or substantially entire length of the cord 220, where the anchor 270 is formed using a portion of the tether 200 and the elongate portion 280 is formed using another portion of the tether, such that the anchor 270 and the elongate portion 280 are formed using a single integral tether 200.

The cord 220 can comprise one or more indentations and/or recesses 260 on at least a portion thereof configured to facilitate migration and/or growth of native tissue cells onto the cord 220. For example, the indentations and/or recesses 260 can be on one or more portions of an externally oriented surface of the cord 220. The one or more indentations and/or recesses 260 can be in a pattern configured to enhance the ability of native heart tissue cells from adjacent portions of the heart to migrate onto the cord 220, thereby facilitating growth of native tissue over the cord 220. The one or more indentations and/or recesses 260 can advantageously enhance cell migration onto and/or proliferation on the cord 220, thereby expediting the regeneration process. In some examples, the one or more indentations and/or recesses 260 can be one or more micropatterns. The micropatterns can be biomimetic micropatterns configured to facilitate cell migration and/or tissue growth over the cord 220. In some examples, the micropatterns can comprise a plurality of grooves, including microgrooves, such as biomimetic microgrooves. In some instances, the one or more indentations and/or recesses 260 can be on an entire or substantially entire length of the cord 220. The one or more indentations and/or recesses 260 can be on an entire or substantially entire length of the cord 220 of the elongate portion 280 and/or anchor 270. For example, indentations and/or recesses 260 can be on all of the externally oriented surface portions of the cord 220 of the elongate portion 280 and/or anchor 270. Alternatively, the one or more indentations and/or recesses 260 can be only on a portion of the length of the cord 220. For example, indentations and/or recesses 260 can be only on a portion of the externally oriented surface of the cord 220 of the elongate portion 280 and/or anchor 270.

In some instances, the cord portions **220*a*, 220*b* of both the tether tails 280*a*, 280*b* can comprise respective indentations and/or recesses 260*a*, 260*b*. The indentations and/or recesses 260*a*, 260*b* can be on externally oriented surface portions of the cord portions 220*a*, 220*b* along the entire or substantially entire length of each of the cord portions 220*a*, 220*b*. In some instances, the cord portion 220C of the anchor 270 can comprise respective indentations and/or recesses 260*c* (not shown). The one or more indentations and/or recesses 260*c* of cord portion 220C can be on externally oriented surface portions along an entire or substantially entire length of the cord portion 220C of the anchor 270. In some instances, the tether 200 can comprise the one or more indentations and/or recesses 260*a*, 260*b* on a part or an entire length of the cord portions 220*a*, 220*b* of the elongate portion 280, without being on any portion of the cord portion 220C of the anchor 270. For example, biomimetic micropatterns can be over all or part of any portion of the cord portions 220*a*, 220*b*, 220C of the elongate portion 280 and/or anchor 270**.

The cord 220 may or may not be biodegradable. In some examples, the cord 220 is not biodegradable. The cord 220 can comprise a non-biodegradable polymer, including expanded polytetrafluoroethylene (ePTFE). The cord 220 can be an expanded polytetrafluoroethylene (ePTFE) suture. The expanded polytetrafluoroethylene (ePTFE) suture can comprise one or more other features as described herein, including for example a plurality of indentations and/or recesses. Native tissue can grow on the expanded polytetrafluoroethylene (ePTFE) suture over time. The native tissue can cover or substantially cover the expanded polytetrafluoroethylene (ePTFE) suture. The expanded polytetrafluoroethylene (ePTFE) suture can remain and provide added durability and/or mechanical strength to the tether 200. For example, regenerated native tissue over the expanded polytetrafluoroethylene (ePTFE) suture can couple a heart valve leaflet to a ventricular portion of the heart wall.

In some examples, the cord 220 can be at least partially biodegradable. The cord 220 can comprise a biodegradable polymer. In some instances, the cord 220 can be entirely biodegradable. For example, the cord 220 can be a biodegradable polymer. The cord 220 can be a synthetic biodegradable polymer. The cord 220 can be a biodegradable polymer suture. The biodegradable polymer can be selected to provide desired strength for tethering the heart valve leaflet to the heart wall, while having a predetermined degradation rate based at least in part on the rate of native tissue growth on the cord 220. In some instances, the cord 220 can be fully biodegradable such that native tissue can grow on and replace the cord 220, such that regenerated native tissue couples a heart valve leaflet to a ventricular portion of the heart wall without or substantially without any portion of the cord 220 remaining.

A composition of a tissue ingrowth promoting coating as described herein can be selected to facilitate migration and/or tissue growth onto the respective substrate, such as the surgical pad no or the cord 220. The tissue ingrowth promoting coating 150 of the surgical pad no and/or the tissue ingrowth promoting coating 250 of the tether 200 can comprise one or more proteins, including animal and/or insect proteins. The protein coating can be configured to confer the biochemical cues for native tissue cells to migrate onto, grow on, and produce extracellular matrix (ECM) for additional growth of native tissue cells thereon, such that native tissue cells can gradually provide at least a part of the tether for the heart valve leaflet. The protein can comprise an extracellular matrix (ECM) protein. In some instances, the protein can comprise one or more of collagen, fibronectin and laminin. In some instances, the protein can comprise a spider protein. In some instances, the protein can comprise a synthetic animal protein. The tissue ingrowth promoting coating 150 of the surgical pad no and the tissue ingrowth promoting coating 250 of the tether 200 can have the same or different composition.

Figure 5:
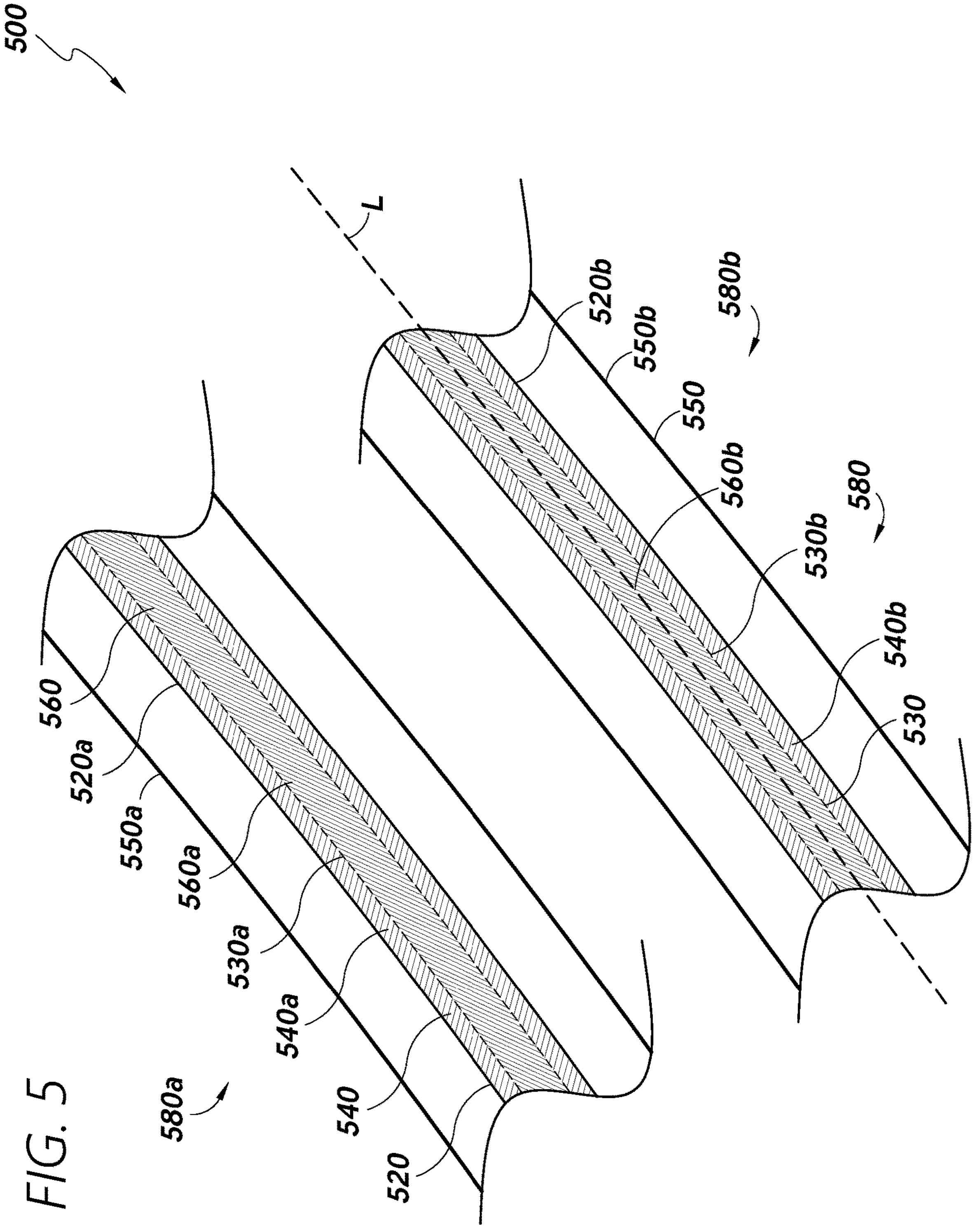
FIG. 5 is a perspective view of a portion of a tether, according to some instances.

FIG. 5 shows an example of a portion of a tether 500 comprising a cord 520 configured to have a non-uniform degradation rate. The degradation rate of the cord 520 can vary along a lateral dimension of the cord 520. The lateral dimension can be perpendicular or substantially perpendicular to a longitudinal axis of the cord 520. The longitudinal axis is shown as the axis "L" in FIG. 5. The degradation rate of the cord 520 can increase along the lateral dimension in a direction from a center to an outer edge of the cord 520. In some instances, the lateral dimension can extend radially from the center of the cord 520 along a direction perpendicular or substantially perpendicular to the longitudinal axis. In some instances, the cord 520 can comprise a plurality of distinct concentric portions where each has a different degradation rate. A concentric portion can have a slower degradation rate than another concentric portion that is further away from the center of the cord 520. For example, an inner portion of the cord 520 can degrade more slowly than an outer portion of the cord 520. As native tissue migrate onto, and/or grow over and/or onto, the cord 520, the outer portion of the cord 520 can degrade, leaving the inner portion of the cord 520 in place. As native tissue further migrates onto, and/or grow over and/or onto, and form tethering between a heart valve leaflet and a ventricular wall portion, the inner portion of the cord 520 can degrade and be replaced by the native tissue. The varying degradation rates of the cord 520 can facilitate replacement of the cord 520 by the native tissue, for example providing allowing a physical structure to remain and guide the migration and/or growth of the native tissue as the native tissue replaces the cord 520 as a tether.

In some instances, a core portion 530 of the cord 520 can have a degradation rate slower than that of an outer layer 540 of the cord 520. For example, the core portion 530 can be a center portion of the cord 520 extending along the longitudinal axis of the cord 520. The outer layer 540 can comprise a portion of the cord 520 disposed over and around the core portion 530. The outer layer 540 can be a portion of the cord 520 concentric with the core portion 530. The outer layer 540 can completely surround and/or wrap around an outer circumference of the core portion 530. In some instances, the cord 520 can have two degradation rates, such as the degradation rate of the core portion 530 and that of the outer layer 540. In some instances, the core portion 530 and the outer layer 540 can extend along an entire or substantially entire length of the cord 520.

Only a portion of an elongate portion 580 of the tether 500 is shown in FIG. 5 for simplicity. For example, an anchor associated with a distal portion of the elongate portion 580 is not shown. The elongate portion 580 can comprise two tether tails 580*a*, 580*b*. Each of the tether tails 580*a*, 580*b* can comprise a respective cord portion 520*a*, 520*b* extending along an entire or substantially entire length thereof. An inner portion of the cord portion 520*a*, 520*b* can have a degradation rate that is slower than an outer portion of the cord portion 520*a*, 520*b*. For example, each of the cord portions 520*a*, 520*b* can have a respective core portion 530*a*, 530*b* extending along an entire or substantially entire length thereof. A respective outer layer 540*a*, 540*b* can surround the core portions 530*a*, 530*b* along an entire or substantially entire length thereof. The core portions 530*a*, 530*b* can have a degradation rate slower than that of a respective outer layer 540*a*, 540*b* of the cord portions 520*a*, 520*b*. The outer layers 540*a*, 540*b* can extend along the entire length of the respective cord portions 520*a*, 520*b* and wrap around corresponding core portions 530*a*, 530*b*. The outer layers 540*a*, 540*b* can have a degradation rate the same as or similar to one another. The core portions 530*a*, 530*a* can have a degradation rate the same as or similar to one another. As native tissue migrates onto and grow over the tether tails 580*a*, 580*b*, outer portions of the cord portions 520*a*, 520*b* can degrade, leaving inner portions of the cord portions 520*a*, 520*b*.

It will be understood that although only two layers of the cord 520 are described with reference to FIG. 5, a cord can have more layers having different degradation rates. For example, the cord 520 can comprise one or more intervening concentric portions between the core portion 530 and the outer layer 540, each of the intervening concentric portions with a different degradation rate. In some examples, the cord 520 can comprise a biodegradable polymeric material. The composition of the polymeric material can be selected to provide the desired degradation gradient along the lateral dimension. The cord 520 can be a polymeric cord comprising a composition selected to provide the desired degradation gradient along the lateral dimension.

The tether 500 can one or more other characteristics of the tether 200 described with reference to FIGS. 2 through 4. For example, the tether 500 can comprise a tissue ingrowth promoting coating 550. Each of the tether tails 580*a*, 580*b* can comprise a respective tissue ingrowth promoting coating portions 550*a*, 550*b*. The tissue ingrowth promoting coating portions 550*a*, 550*b* can be on a respective outer layer 540*a*, 540*b* of the cord portions 520*a*, 520*b*. In some instances, the tissue ingrowth promoting coating 550 can be on a cord portion of the anchor (not shown). The tissue ingrowth promoting coating 550 can have one or more characteristics as described herein. In some instances, the cord 520 can comprise one or more indentations and/or recesses 560 on at least a portion thereof. In some examples, the cord portions 520*a*, 520*b* can each comprise a plurality of indentations and/or recesses 560*a*, 560*b*, such as biomimetic micropatterns, including biomimetic microgrooves, thereon. The biomimetic micropatterns can be along an entire or substantially entire length of each of the cord portions 520*a*, 520*b*. In some instances, the cord portion of the anchor of the tether 500 can comprise a plurality of biomimetic micropatterns, including biomimetic microgrooves, thereon. The one or more indentations and/or recesses 560 can have one or more characteristics as described herein. The anchor and the elongate portion 580 can be a unitary piece. In some instances, the cord portion forming the anchor can comprise a varying degradation rate along a lateral dimension of the cord portion. For example, the core portion 530 and the outer layer 540 can extend along an entire or substantially entire length of the cord 520 such that the cord portion of the anchor can comprise a respective core portion and outer layer.

Figure 6:
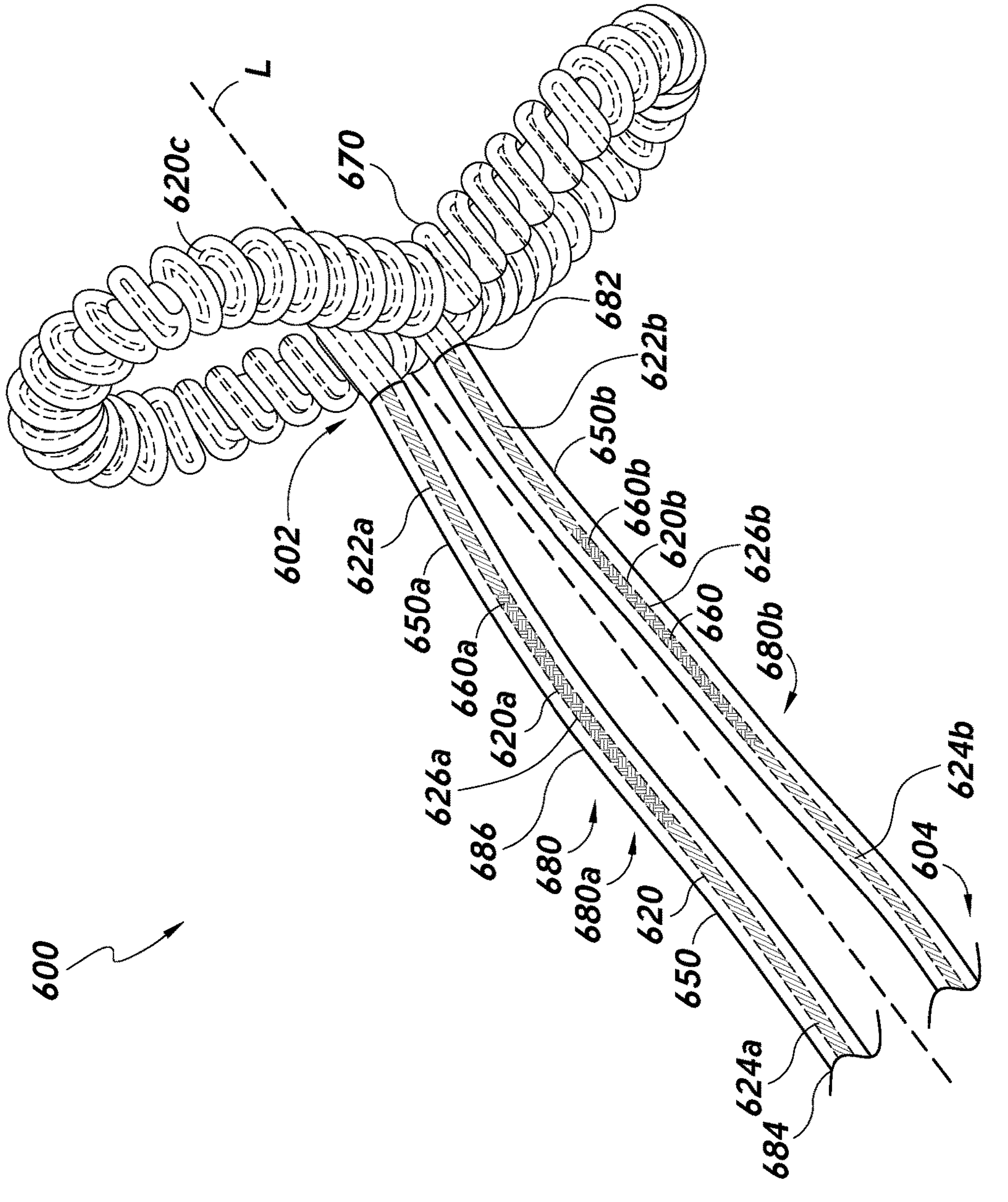
FIG. 6 is a perspective view of another tether, according to some instances.

FIG. 6 shows an example of another tether 600 comprising a cord 620 which can have a non-uniform degradation rate. The tether 600 is shown in a deployed configuration. The cord 620 can have a degradation rate which varies along a longitudinal axis of the tether 600 in the deployed state. The longitudinal axis is shown as the axis "L" in FIG. 6. For example, a degradation rate of a portion of the cord 620 can depend upon a position of the portion along the longitudinal axis of the tether 600 while the tether 600 is in the deployed state. A cord portion configured to be positioned closer to native tissue while in the deployed state can have a degradation rate faster than that of a cord portion further away from the native tissue.

A distal portion 602 of the tether 600 can comprise an anchor 670. The distal portion 602 can be configured to be coupled to a heart valve leaflet. A proximal portion 604 of the tether 600 can be configured to be coupled to a heart ventricular wall. The tether 600 can comprise an elongate portion 680 coupled to the anchor 670. The elongate portion 680 can comprise at least a portion configured to extend between a heart valve leaflet and a heart wall portion. Portions of the elongate portion 680 configured to be closer to native tissue while the tether 600 is in the deployed state can have a faster degradation rate than that of portions further away from native tissue. In some instances, first and second end portions of the elongate portion 680 configured to be closer to native while the tether 600 is in the deployed state can degrade at a faster rate than a middle portion between the first and second end portions. For example, a proximal portion 684 of the elongate portion 680 configured to be proximate and/or adjacent to ventricular heart wall tissue, and a distal portion 682 of the elongate portion 680 configured to be proximate and/or adjacent to heart valve leaflet tissue, can degrade more quickly than a middle portion 686 further away from the ventricular wall tissue and heart valve leaflet tissue. A cord 620 can extend through at least a portion of the tether 600, including the elongate portion 680 and/or the anchor 670. In some instances, the tether 600 can comprise the cord 620 extending through an entire or substantially entire length thereof. The elongate portion 680 can comprise two tether tails 680*a*, 680*b*. Each of the tether tails 680*a*, 680*b* can comprise a respective cord portion 620*a*, 620*b*. In some instances, the cord 620 can extend through the entirety or substantially entirety of the elongate portion 680. For example, cord portions 620*a*, 620*b* can extend through an entire or substantially entire length of the tether tails 680*a*, 680*b*. Portions of the cord 620 configured to be positioned closer to native tissue while the tether 600 is in the deployed state can have degradation rates faster than those of portions further away from the native tissue. For example, degradation rates of respective middle portions 626*a*, 626*b* of the cord portions 620*a*, 620*b* can be slower than those of respective proximal portions 624*a*, 624*b* and distal portions 622*a*, 622*b* of the cord portions 620*a*, 620*b*. The middle portions 626*a*, 626*b* can be further away from native tissue when the tether 600 is deployed at its target site, while the proximal portions 624*a*, 624*b* and distal portions 622*a*, 622*b* are closer to native tissue. For example, the proximal portions 624*a*, 624*b* can be oriented toward, and be adjacent and/or proximate to ventricular wall tissue. The distal portions 622*a*, 622*b* can be oriented toward, and be adjacent and/or proximate to heart valve leaflet tissue. Tissue growth over the proximal portions 624*a*, 624*b* and distal portions 622*a*, 622*b* can occur earlier as native tissue migrates onto the cord portions 620*a*, 620*b* initially along the proximal portions 624*a*, 624*b* and distal portions 622*a*, 622*b* prior to reaching the middle portions 626*a*, 626*b*. The proximal portions 624*a*, 624*b* and the distal portions 622*a*, 622*b* can degrade and/or be consumed first as the regenerated native tissue first form the proximal and distal portions of the tethering between the heart valve leaflet and the heart wall. At least a portion of the middle portions 626*a*, 626*b* can remain while the native tissue continue to migrate onto and/or grow on the middle portions 626*a*, 626*b*.

The proximal portions 624*a*, 624*b* can have a degradation rate the same as or similar to one another. The distal portions 622*a*, 622*b* can have a degradation rate the same as or similar to one another. The middle portions 626*a*, 626*b* can have a degradation rate the same as or similar to one another. In some instances, the proximal portions 624*a*, 624*b* and the distal portions 622*a*, 622*b* can have a degradation rate the same as or similar to one another. The proximal portions 624*a*, 624*b* and distal portions 622*a*, 622*b* can degrade at a faster rate as native tissue initially migrate onto and grow over the proximal portions 624*a*, 624*b* and distal portions 622*a*, 622*b*, leaving the middle portions 626*a*, 626*b*.

In some instances, the cord 620 can extend through at least a portion of the anchor 670, including the entirety or substantially entirety of the anchor 670. For example, the anchor 670 can comprise a cord portion 620*c* extending therethrough. In some instances, the cord portion 620*c* can be biodegradable.

In some instances, the cord portions 620*a*, 620*b*, 620*c* can comprise a biodegradable polymeric material. The composition of the polymeric material can be selected to provide the desired degradation gradient along the longitudinal axis. The cord portions 620*a*, 620*b* can be polymeric suture portions comprising a composition selected to provide the desired degradation gradient along the longitudinal axis. Although FIG. 6 describes the cord portions 620*a*, 620*b* of the elongate portion 680 as each comprising three segments having corresponding degradation rates, a cord portion can have more or fewer segments having different degradation rates.

The tether boo can one or more other characteristics of the tether 200 described with reference to FIGS. 2 through 4. For example, the tether 600 can comprise a tissue ingrowth promoting coating 650. Each of the tether tails 680*a* can comprise a respective tissue ingrowth promoting coating portion 650*a*, 650*b*. The tissue ingrowth promoting coating portions 650*a*, 650*b* can have one or more characteristics as described herein. In some instances, the cord 620 can comprise one or more indentations and/or recesses 660 on at least a portion thereof. In some examples, the cord portions 620*a*, 620*b* can each comprise indentations and/or recesses 660*a*, 660*b*, such as a plurality of biomimetic micropatterns, including biomimetic microgrooves, thereon. The indentations and/or recesses 660*a*, 660*b* can be along an entire or substantially entire length thereof. In some instances, the cord portion 620*c* of the anchor 670 can comprise a plurality of biomimetic micropatterns, including biomimetic microgrooves, thereon. The one or more indentations and/or recesses 660 can have one or more characteristics as described herein.

Figure 7:
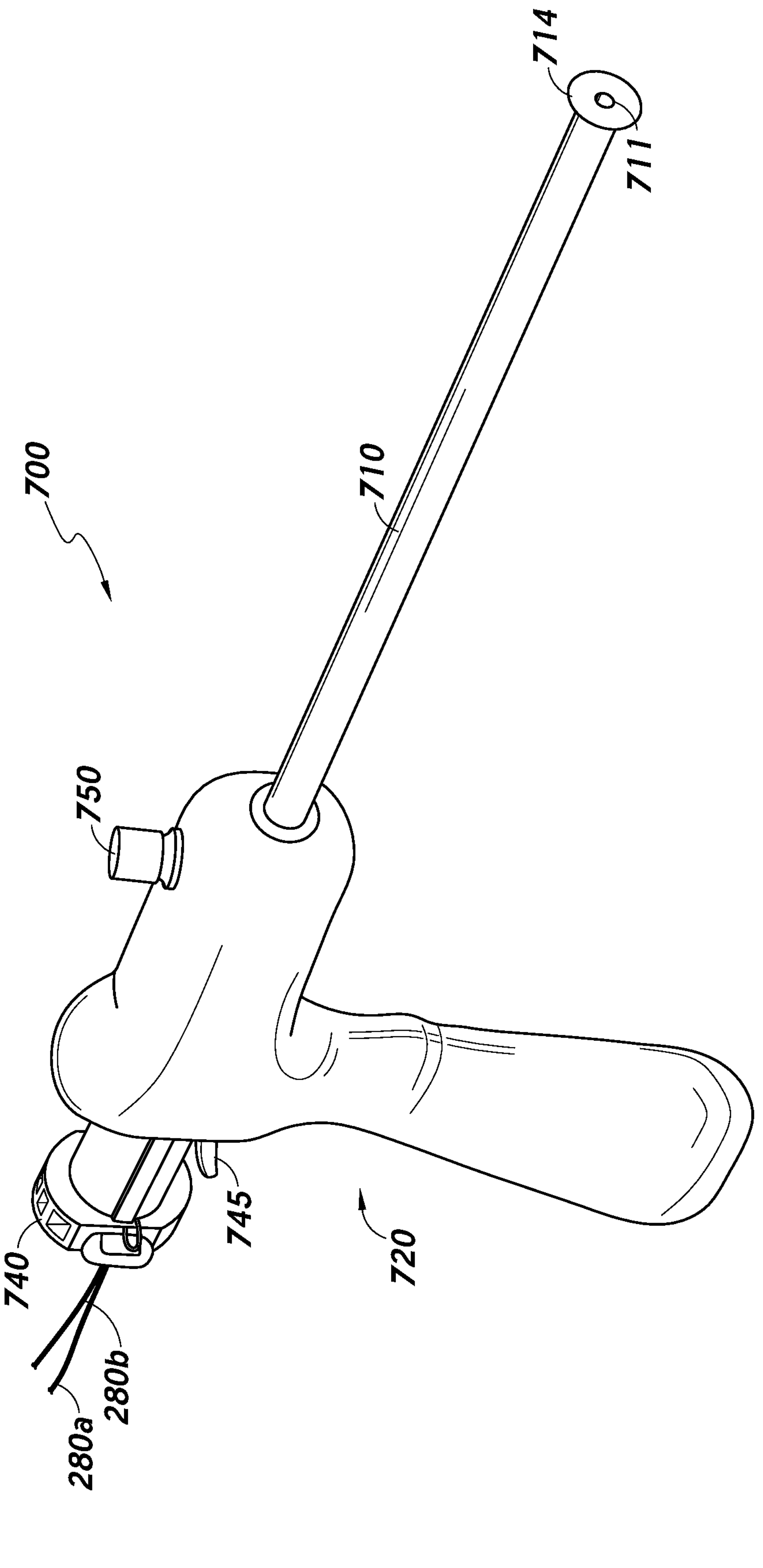
FIG. 7 is a perspective view of a tether delivery system, according to some instances.

FIG. 7 is a perspective view of a tether delivery system 700 in accordance with one or more examples. The delivery system 700 may be used to deploy one or more tethers as described herein, such as to repair a heart valve, including a mitral valve, and improve functionality thereof. The delivery system 700 can be used to deliver the tether 200. Various parts of an example of a delivery process are described with reference to FIGS. 8A-8E below. For example, the delivery system 700 may be used to reduce the degree of mitral regurgitation in patients suffering from mitral regurgitation. Mitral regurgitation can be caused by, but are not limited to, midsegment prolapse of valve leaflets as a result of degenerative mitral valve disease. In order to repair such a valve, the delivery system 700 may be utilized to deliver and anchor tissue anchors, such as suture-knot-type tissue anchors, in a prolapsed valve leaflet. As described in detail below, such a procedure may be implemented on a beating heart.

The delivery system 700 can include an elongate rigid tube 710 forming at least one internal working lumen. Although described in certain examples and/or contexts as comprising an elongate rigid tube, it should be understood that tubes, shafts, lumens, conduits, and the like disclosed herein may be either rigid, at least partially rigid, at least flexible, and/or at least partially flexible. Therefore, any such component described herein, whether or not referred to as rigid herein should be interpreted as possibly being at least partially flexible.

In addition to the elongate rigid tube 710, the delivery system 700 may include a plunger 740, which may be used or actuated to manually deploy the tether. The delivery system 700 may further include a plunger lock mechanism 745, which may serve as a safety lock that locks the delivery system 700 until ready for use or deployment of a tether as described herein. The plunger 740 may have associated therewith a suture-release mechanism, which may be configured to lock in relative position a pair of tether tails 280*a*, 280*b* associated with a pre-formed knot anchor (not shown) to be deployed. The delivery system 700 may further comprise a flush port 750, which may be used to de-air the lumen of the elongate rigid tube 710. For example, heparinized saline flush, or the like, may be connected to the flush port 750 using a female Luer fitting to de-air the delivery system 700. The term "lumen" is used herein according to its broad and ordinary meaning, and may refer to a physical structure forming a cavity, void, pathway, or other channel, such as an at least partially rigid elongate tubular structure, or may refer to a cavity, void, pathway, or other channel, itself, that occupies a space within an elongate structure (e.g., a tubular structure). Therefore, with respect to an elongate tubular structure, such as a shaft, tube, or the like, the term "lumen" may refer to the elongate tubular structure and/or to the channel or space within the elongate tubular structure.

The lumen of the elongate rigid tube 710 may house a needle (not shown) that is wrapped at least in part with a pre-formed knot sutureform anchor, as described in detail herein. In some examples, the elongate rigid tube 710 presents a relatively low profile. For example, the elongate rigid tube 710 may have a diameter of about 3 millimeters (mm) or less (e.g., about 9 French (Fr) or less). The elongate rigid tube 710 is associated with an atraumatic tip 714 feature. The atraumatic tip 714 can be an echogenic leaflet-positioner component, which may be used for deployment and/or positioning of the suture-type tissue anchor. The atraumatic tip 714, disposed at and/or coupled to the distal end of the elongate rigid tube 710, may be configured to have deployed therefrom a wrapped pre-formed suture knot (e.g., sutureform), as described herein.

The atraumatic tip 714 may be referred to as an "end effector." In addition to housing a pre-formed knot sutureform and associated needle, the elongate rigid tube 710 may house an elongated knot pusher tube (not shown; also referred to herein as a "pusher"), which may be actuated using the plunger 740 in some examples. As described in further detail below, the atraumatic tip 714 provides a surface against which the target valve leaflet may be held in connection with deployment of a leaflet anchor.

The delivery system 700 may be used to deliver a "bulky knot" type tissue anchor, as described in greater detail below. For example, the delivery system 700 may be utilized to deliver an anchor as described herein (e.g., bulky knot, such as the anchor 270 described with reference to FIG. 2) onto a distal side of a mitral valve leaflet. The atraumatic tip 714 (e.g., end effector), can be placed in contact with a leaflet of a mitral valve. The atraumatic tip 714 can be coupled to the distal end portion of the elongate rigid tube 710, wherein the proximal end portion of the elongate rigid tube 710 may be coupled to a handle 700 of the delivery system 700, as shown. Generally, the elongate pusher (not shown) may be movably disposed within a lumen of the elongate rigid tube 710 and coupled to a pusher hub (not shown) that is movably disposed within the handle 720 and releasably coupled to the plunger 740. A needle (not shown) carrying a pre-formed tissue anchor sutureform can be movably disposed within a lumen of the pusher and coupled to a needle hub (not shown) that is also coupled to the plunger 740. The plunger 740 can be used to actuate or move the needle and the pusher during deployment of a distal anchor (see, e.g., FIGS. 8C and 8D) and is movably disposed at least partially within the handle 720. For example, the handle 720 may define a lumen in which the plunger 740 can be moved. During operation, the pusher may also move within the lumen of the handle 720. The plunger lock 745 can be used to prevent the plunger 740 from moving within the handle 720 during storage and prior to performing a procedure to deploy a tissue anchor.

The needle may have the pre-formed knot disposed about a distal portion thereof while maintained in the elongate rigid tube 710. For example, the pre-formed knot sutureform may be formed of one or more sutures configured in a coiled sutureform (see FIG. 8C) having a plurality of winds/turns around the needle over a portion of the needle that is associated with a longitudinal slot in the needle that runs from the distal end thereof. The coiled sutureform may advantageously be configured to be formed into a suture-type tissue anchor (referred to herein as a "bulky knot") in connection with an anchor-deployment procedure, as described in more detail below. The coiled sutureform can be configurable to a knot/deployed configuration by approximating opposite ends of the coiled portion thereof towards each other to form one or more loops. For example, the pre-formed knot sutureform can be used to form at least a portion of the anchor 270. Although the term "sutureform" is used herein, it should be understood that such components/forms may comprise suture, wire, or any other elongate material wrapped or formed in a desired configuration. The coiled sutureform can be provided or shipped disposed around the needle. In some examples, two tether tails extend from the coiled sutureform. The tether tails 280*a*, 280*b* may extend through the lumen of the needle and/or through a passageway of the plunger 740 and may exit the plunger 740 at a proximal end portion thereof.

The delivery device can further include a suture/tether catch mechanism (not shown) coupled to the plunger 740 at a proximal end of the delivery system 700, which may be configured to releasably hold or secure the tether 200 extending through the delivery system 700 during delivery of a tissue anchor as described herein. The suture catch can be used to hold the tether 200 with a friction fit or with a clamping force and can have a lock that can be released after the tissue anchor has been deployed/formed into a bulky knot, as described herein.

As described herein, the delivery system 700 can be used in beating heart mitral valve repair procedures. In some examples, the elongate rigid tube 710 of the delivery system 700 can be configured to extend and contract with the beating of the heart. During systolic contraction, the median axis of the heart generally shortens. For example, the distance from the apex 18 of the heart to the valve leaflets 62, 64 can vary by about 1 centimeter (cm) to about 2 centimeters (cm) with each heartbeat in some patients. In some examples, the length of the elongate rigid tube 710 that protrudes from the handle 720 can change with the length of the median axis of the heart. That is, distal end of the elongate rigid tube 710 can be configured to be floating such that the shaft can extend and retract with the beat of the heart so as to maintain contact with the target mitral valve leaflet.

Implementation of a valve-repair procedure utilizing the delivery system 700 can be performed in conjunction with certain imaging technology designed to provide visibility of the elongate rigid tube 710 according to a certain imaging modality, such as echo imaging. Advancement of the delivery system 700 may be performed in conjunction with echo imaging, direct visualization (e.g., direct transblood visualization), and/or any other suitable remote visualization technique/modality. With respect to cardiac procedures, for example, the delivery system 700 may be advanced in conjunction with transesophageal (TEE) guidance and/or intracardiac echocardiography (ICE) guidance to facilitate and to direct the movement and proper positioning of the device for contacting the appropriate target cardiac region and/or target cardiac tissue (e.g., a valve leaflet, a valve annulus, or any other suitable cardiac tissue). Typical procedures that can be implemented using echo guidance are set forth in Suematsu, Y., *J. Thorac. Cardiovasc. Surg.* 2005; 130:1348-56 ("Suematsu"), the entire disclosure of which is incorporated herein by reference.

Figure 8A:
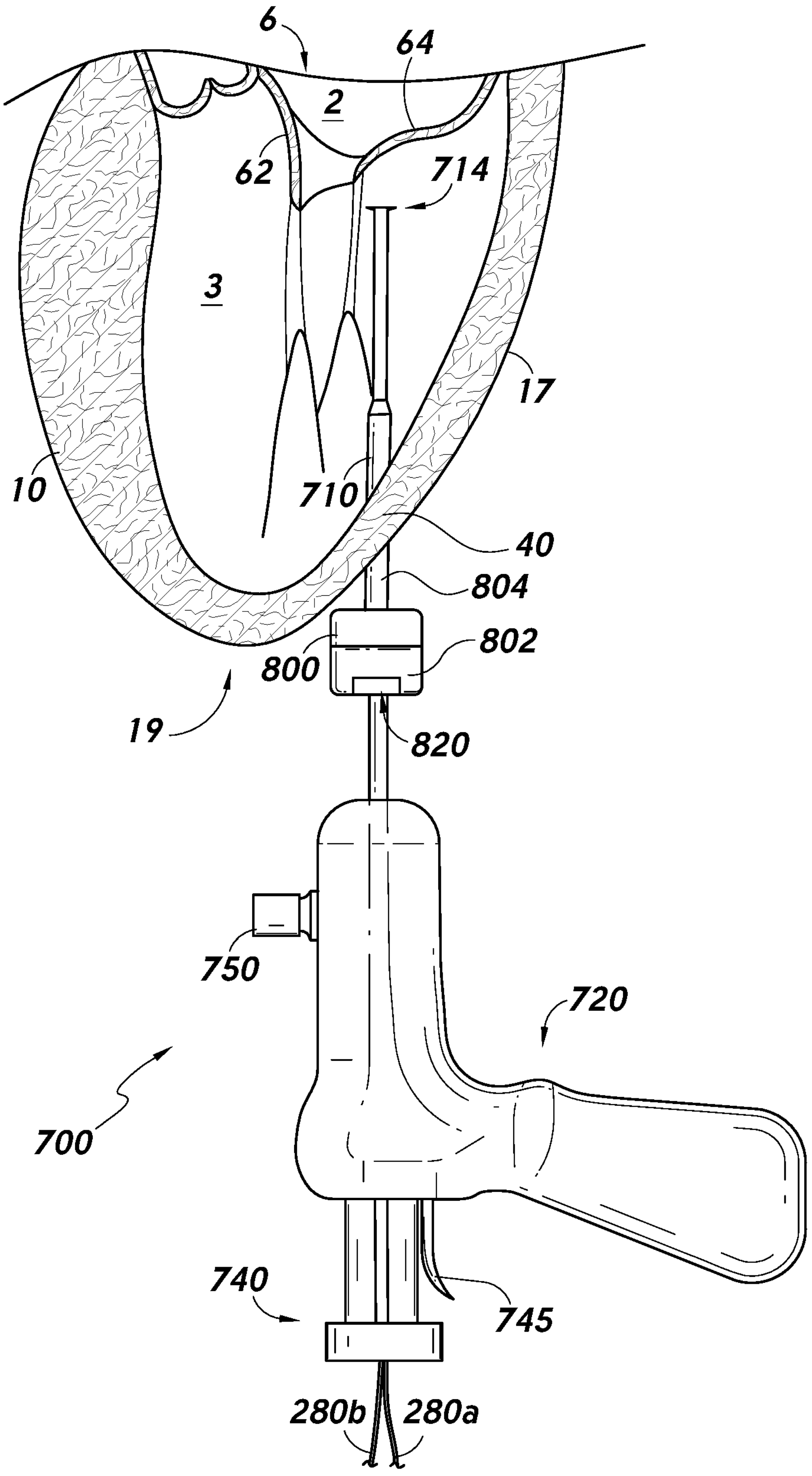
FIGS. 8A, 8B, 8C, 8D and 8E show various steps of deploying a tether using the tether delivery system described with reference to FIG. 7, according to some instances.

FIGS. 8A through 8E show various steps for delivering the tether 200 using the tether delivery system 700 described with reference to FIG. 7. FIG. 8A is a cutaway view of a chamber of a heart and the delivery system 700 disposed at least partially within the chamber of the heart in accordance with one or more examples. According to some implementations of valve-repair procedures, an incision into the apical region 19 of the appropriate ventricle of the heart is made. FIG. 8A shows the delivery system 700 at least partially positioned within the left ventricle 3. For instance, an introducer port device 800 can be used to facilitate advancement of at least a portion of the elongate rigid tube 710 into the left ventricle 3. The introducer port device 800 can comprise an introducer hub 802 containing one or more fluid-retention valves to prevent blood loss and/or air entry into the left ventricle 3. An introducer shaft 804 can extend distally from the introducer hub 802. At least a portion of the introducer shaft 804 may be inserted into the site of entry. The elongate rigid tube 710 may be advanced through a lumen 820 of the introducer port device 800 that extends through the introducer hub 802 and the introducer shaft 804. For example, the lumen 820 can be in fluid communication with one or more of the fluid-retention valves such that the fluid-retention valves can prevent or reduce blood loss and/or air entry around portions of the elongate rigid tube 710 positioned therethrough. In some examples, a sheath may be inserted through the introducer port device 800, through which one or more other instruments are advanced. For instance, an endoscope may first be advanced into the left ventricle 3 through the introducer port device 800 to visualize the ventricle, the mitral valve 6, and/or the subvalvular apparatus. By use of an appropriate endoscope, a careful analysis of the malfunctioning mitral valve 6 may be performed. Each segment of each leaflet may be carefully assessed to determine its pliability, integrity, and motion. Based on this assessment, the practitioner can determine whether the valve can indeed be repaired or must be replaced. The motion of the leaflets 62, 64 can be classified as slightly dysfunctional, prolapsed, or restricted and based on this classification, the necessary steps of the repair can be determined.

After a minimally invasive approach is determined to be advisable, one or more incisions may be made proximate to the thoracic cavity to provide a surgical field of access. The total number and length of the incisions to be made depend on the number and types of the instruments to be used as well as the procedure(s) to be performed. The incision(s) may advantageously be made in such a manner as to be minimally invasive. As referred to herein, the term "minimally invasive" means in a manner by which an interior organ or tissue may be accessed with relatively little damage being done to the anatomical structure through which entry is sought. For example, a minimally invasive procedure may involve accessing a body cavity by a small incision/opening of, for example, about 5 centimeters (cm) or less made in the skin of the body. The incision may be vertical, horizontal, or slightly curved. If the incision is located along one or more ribs, it may advantageously follow the outline of the rib. The opening may advantageously extend deep enough to allow access to the thoracic cavity between the ribs or under the sternum and is preferably set close to the rib cage and/or diaphragm, dependent on the entry point chosen.

In one example method, the heart may be accessed through one or more openings made by one or more small incision in a portion of the body proximal to the thoracic cavity, such as between one or more of the ribs of the rib cage of a patient, proximate to the xyphoid appendage, or via the abdomen and diaphragm. Access to the thoracic cavity may be sought to allow the insertion and use of one or more thorascopic instruments, while access to the abdomen may be sought to allow the insertion and use of one or more laparoscopic instruments. Insertion of one or more visualizing instruments may then be followed by transdiaphragmatic access to the heart. Additionally, access to the heart may be gained by direct puncture (e.g., via an appropriately sized needle, for instance an 18-gauge needle) of the heart from the xyphoid region. Accordingly, the one or more incisions should be made in such a manner as to provide an appropriate surgical field and access site to the heart in the least invasive manner possible. Access may also be achieved using percutaneous methods, further reducing the invasiveness of the procedure. See, e.g., "Full-Spectrum Cardiac Surgery Through a Minimal Incision Mini-Sternotomy (Lower Half) Technique," Doty et al., *Annals of Thoracic Surgery* 1998; 65(2): 573-7 and "Transxiphoid Approach Without Median Sternotomy for the Repair of Atrial Septal Defects," Barbero-Marcial et al., *Annals of Thoracic Surgery* 1998; 65(3): 771-4, the entire disclosures of each of which are incorporated herein by reference for all purposes.

Figure 8B:
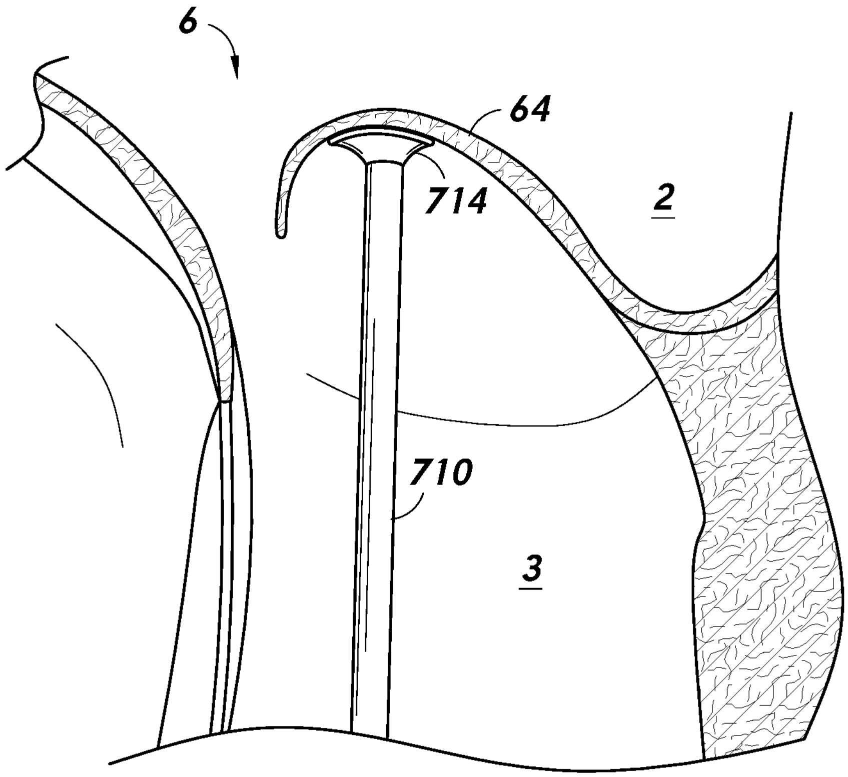
Figure 8D:
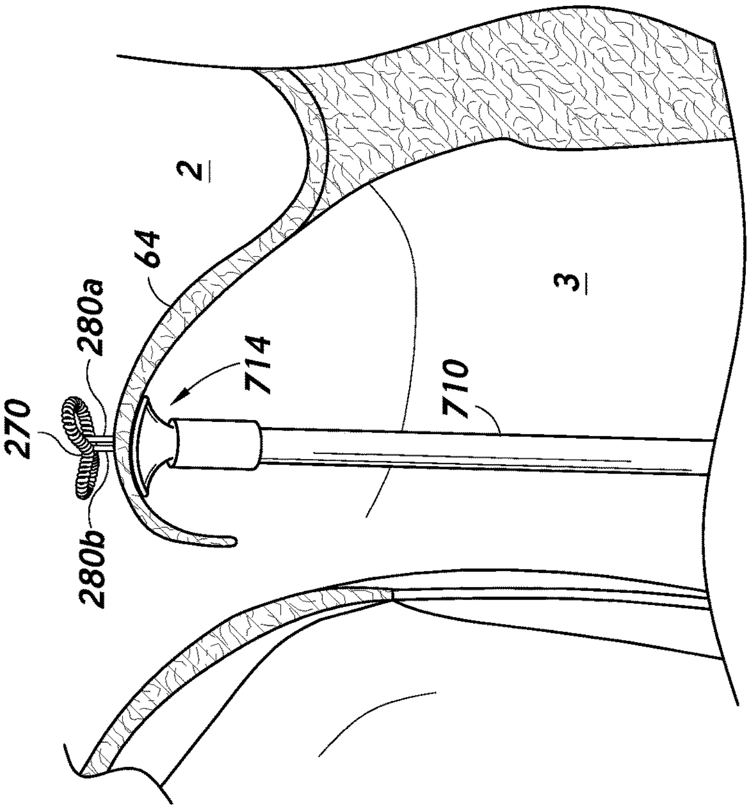
Figure 8C:
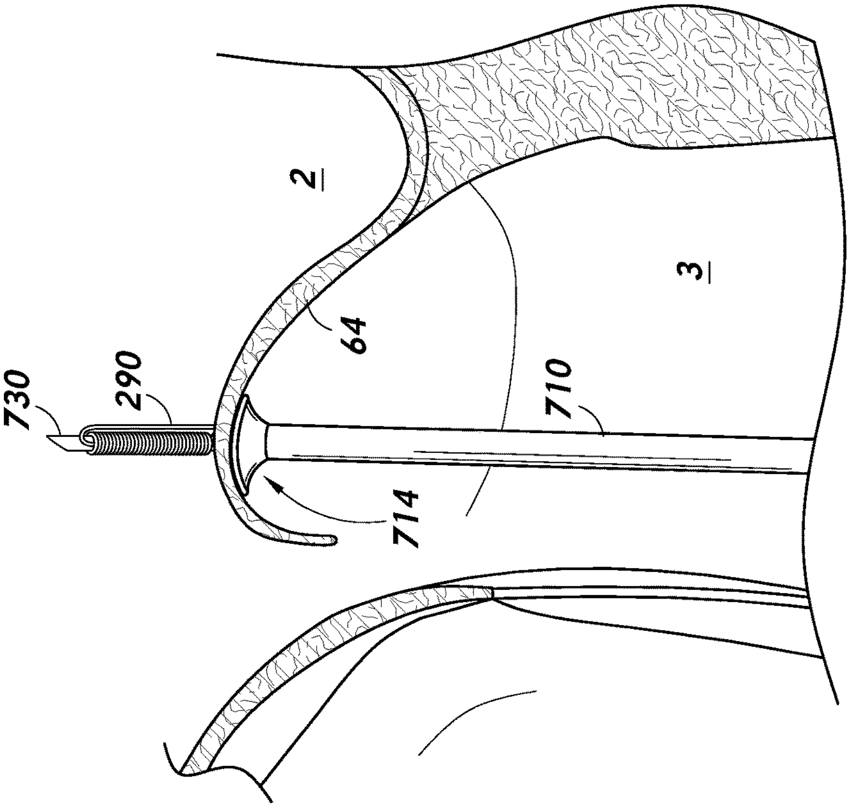

Generally, the elongate rigid tube 710 of the delivery system 700 may be slowly advanced into the introducer port device 800 until the atraumatic tip 714 and/or a needle 730 (e.g., the needle 730 is shown in FIG. 8C) are distal of the introducer port device 800. For example, the elongate rigid tube 710 can be advanced until the atraumatic tip 714 has been advanced through the lumen 820 of the introducer shaft 804 and has entered the left ventricle 3. In so doing, it may be desirable to advance the elongate rigid tube 710 within the left ventricle 3 in such a way as to avoid traversing areas populated by papillary muscles and/or associated chordae tendineae to avoid entanglement therewith. In order to facilitate or ensure avoidance of such anatomy, imaging technology may advantageously be implemented to provide at least partial visibility of the elongate rigid tube 710 within the left ventricle 3, as well as certain anatomical features within the ventricle. In some implementations, hybrid imaging technologies may be used, wherein echo imaging is used in combination with a different imaging modality. Multi-imaging modalities may provide improved visibility of anatomical and/or delivery system components.

Although the procedures described herein are with reference to repairing a cardiac mitral valve or tricuspid valve by the implantation of one or more leaflet anchors and associated suture(s)/cord(s), the methods presented are readily adaptable for various types of tissue, leaflet, and annular repair procedures. The methods described herein, for example, can be performed to selectively approximate two or more portions of tissue to limit a gap between the portions. That is, in general, the methods herein are described with reference to a mitral valve but should not be understood to be limited to procedures involving a mitral valve. Furthermore, aspects of the present disclosure applicable to non-biological structures and devices. For example, other cord or suture tensioning applications not involving biological tissue may incorporate aspects of the pension balancing and/or distribution devices, systems, and processes disclosed herein.

FIG. 8B shows a close-up view of the elongate rigid tube 710 of the delivery system 700 inserted into the left ventricle 3 and approximated to a target valve leaflet 64 in connection with a valve-repair procedure in accordance with one or more examples of the present disclosure. The elongate rigid tube 710 can be configured to deliver a tissue anchor (not shown; see, e.g., FIGS. 8C through 8E), such as a bulky knot, to the valve leaflet 64. As an example, FIG. 8B shows a valve leaflet 64, which may represent a posterolateral leaflet of the mitral valve 6. It will be understood that the elongate rigid tube 710 can also deliver a tissue anchor to the anteromedial mitral valve leaflet. Although the description of FIGS. 8B through 8E below is presented in the context of a mitral valve, it should be understood that the principles disclosed herein are applicable to other valves or biological tissues, such as a tricuspid valve.

With reference to FIGS. 8B through 8E, the elongate rigid tube 710 can comprise one or more elongate lumens configured to allow delivery of the anchor 270 to the valve leaflet 64. The elongate rigid tube 710 can be configured to facilitate performance of one or more functions, such as grasping, suctioning, irrigating, cutting, suturing, or otherwise engaging a valve leaflet. The distal end, such as the atraumatic tip 714, of the elongate rigid tube 710 can be configured to contact the mitral valve leaflet 64 without substantially damaging the leaflet to facilitate repair of the valve 6. For example, during a valve-repair procedure, a handle (e.g., handle 720) coupled to the elongate rigid tube 710 can be manipulated in such a manner so that the leaflet 64 is contacted with the functional distal portion of the elongate rigid tube 710 and a repair can be effectuated.

Echo imaging guidance, such as transesophageal echocardiogram (TEE) (2D and/or 3D), transthoracic echocardiogram (TTE), and/or intracardiac echo (ICE), may be used to assist in the advancement and desired positioning of the elongate rigid tube 710 within the left ventricle 3. The atraumatic tip 714 of the elongate rigid tube 710 can contact a proximal surface (e.g., underside surface with respect to the illustrated orientation of FIGS. 8B through 8E) of the mitral valve leaflet 64, without or substantially without damaging the leaflet 64. For example, the atraumatic tip 714 can have a relatively blunt form or configuration. The atraumatic tip 714 can be configured to maintain contact with the proximal side of the valve leaflet 64 as the heart beats to facilitate reliable delivery of the anchor 270 to the target site on the leaflet 64.

Figure 8E:
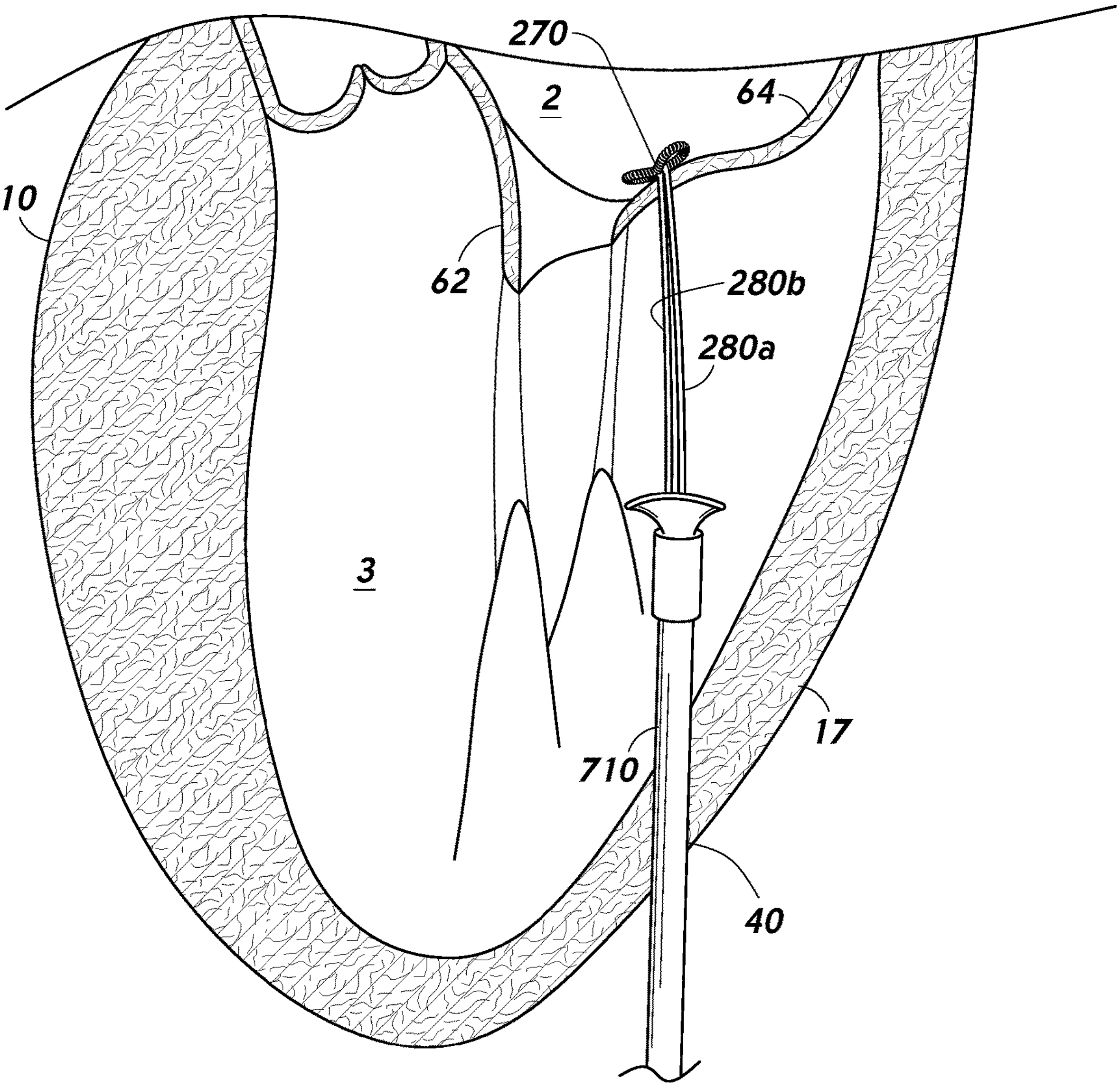

In some examples, one or more perforation devices, such as a needle 730 (e.g., needle(s)) can be delivered through a working lumen (not shown) of the elongate rigid tube 710 to the valve leaflet 64 to puncture the valve leaflet 64 and project a sutureform 290 including a plurality of winds of suture about a distal portion of the needle 730 into the left atrium 2 (see FIG. 8C), wherein the sutureform 290 is deployed to form the bulky knot anchor 270 shown in FIGS. 8D and 8E. For example, referring to FIG. 8C, the needle 730 can be deployed from the distal end of the elongate rigid tube 710, thereby puncturing the leaflet 64 and projecting into the left atrium 2. The needle 730 can comprise a slot and can comprise the sutureform 290 wrapped therearound in a particular configuration (see PCT Application No. PCT/US2012/043761, entitled "Transapical Mitral Valve Repair Device" for further detail regarding example suture wrapping configurations and needles for use in suture anchor deployment devices and methods). In some examples, a pusher or hollow guide wire (not shown) is provided on or at least partially around the needle 730 within the elongate rigid tube 710, such that the needle may be withdrawn, leaving the pusher and wound sutureform 290. When a withdrawal force is applied to the sutureform 290 using the pusher, the sutureform 290 may form a bulky-knot-type anchor (e.g., the anchor 270), after which the pusher may be withdrawn, leaving the bulky-knot-type anchor to anchor the tether tails 280*a*, 280*b* to the leaflet 64.

FIG. 8B shows the elongate rigid tube 710 of the delivery system 700 positioned on the mitral valve leaflet 64. For example, the target site of the mitral valve leaflet 64 may be slowly approached from the ventricle side thereof by advancing the distal end of elongate rigid tube 710 along or near to the posterior wall of the left ventricle 3 without contacting the ventricle wall. Successful targeting and contacting of the target location on the leaflet 64 can depend at least in part on accurate visualization of the elongate rigid tube 710 and/or atraumatic tip 714 throughout the process of advancing the atraumatic tip 714 to the target site. Generally, echocardiographic equipment may be used to provide the necessary or desired intra-operative visualization of the elongate rigid tube 710 and/or atraumatic tip 714.

Once the atraumatic tip 714 is positioned in the desired position, the distal end of the elongate rigid tube 710 and the atraumatic tip 714 may be used to drape, or "tent," the mitral valve leaflet 64 to better secure the atraumatic tip 714 in the desired position, as shown in FIG. 8B. Draping/tenting may advantageously facilitate contact of the atraumatic tip 714 with the leaflet 64 throughout one or more cardiac cycles, to thereby provide more secure or proper deployment of leaflet anchor(s). The target location may advantageously be located relatively close to the free edge of the mitral valve leaflet 64 to minimize the likelihood of undesirable intra-atrial wall deployment of the anchor. Navigation of the atraumatic tip 714 to the desired location on the underside of the mitral valve leaflet 64 may be assisted using echo imaging, which may be relied upon to confirm correct positioning of the atraumatic tip 714 prior to anchor/knot deployment.

After the atraumatic tip 714 is desirably positioned on the underside of the mitral valve leaflet 64, the plunger 740 can be actuated and a distal piercing portion of the needle 730 can puncture the leaflet 64 to form an opening in the leaflet 64. FIG. 8C shows a close-up view of the distal portion of the elongate rigid tube 710 showing the needle 730 and tissue anchor sutureform 290 projected therefrom through the mitral valve leaflet 64 in accordance with one or more examples. In some examples, the needle 730, such as a distal end of the needle 730, is projected a distance of between about 0.2 to about 0.3 inches (about 5 to about 8 millimeters (mm)), or less, distally beyond the distal end of the elongate rigid tube 710 (e.g., beyond the atraumatic tip 714). In some examples, the needle 730 is projected a distance of between about 0.15 to about 0.4 inches (about 4 to about 10 millimeters (mm)). In some examples, the needle 730 is projected a distance of about 1 inch (about 25 millimeters (mm)), or greater. In some examples, the needle 730 extends until the distal end of the needle 730 and the entire coiled sutureform 290 extend through the leaflet 64. While the needle 730 and sutureform 290 are projected into the side of the leaflet 64 oriented toward the left atrium 2, the elongate rigid tube 710 and atraumatic tip 714 advantageously remain entirely on the side of the leaflet 64 oriented toward the left ventricle 3.

With the elongate rigid tube 710 positioned against the mitral valve leaflet 64, the plunger 740 of the delivery system 700 can be actuated to move the needle 730 and a pusher disposed within the elongate rigid tube 710, such that the coiled sutureform portion 290 of the suture anchor slides off the needle 730. As the pusher (not shown) within the tissue anchor delivery device elongate rigid tube 710 is moved distally, a distal end of the pusher advantageously moves or pushes the distal coiled sutureform 290 (e.g., pre-deployment coiled portion of the suture anchor) over the distal end of the needle 730 and further within the left atrium 2 of the heart on a distal side of the mitral valve leaflet 64, such that the sutureform 290 extends distally beyond a distal end of the needle 730. For example, in some examples, at least half a length of the sutureform 290 extends beyond the distal end of the needle 730. In some examples, at least three quarters of the length of the sutureform 290 extends beyond the distal end of the needle 730. In some examples, the entire coiled sutureform 290 extends beyond the distal end of the needle 730.

After the sutureform 290 has been pushed off the needle 730, pulling one or more of the tether tail(s) 280*a*, 280*b* (e.g., strands extending from the coiled portion of the tether) associated with the tissue anchor 270 proximally can cause the sutureform 290 to form the anchor 270 (e.g., a bulky knot anchor), as shown in FIG. 8D, which provides a close-up view of the formed anchor 270 on the side of the leaflet 64 oriented toward the left atrium 2. For example, the bulky knot suture anchor may be formed by approximating opposite ends of the coils of the sutureform 290 (see FIG. 8C) towards each other to form one or more loops. After the sutureform 290 has been formed into the bulky knot, the delivery system 700 can be withdrawn proximally, leaving the anchor 270 disposed on the distal atrial side of the leaflet 64.

FIG. 8E shows a cutaway view of the heart with the deployed leaflet anchor 270 and the elongate rigid tube 710 being withdrawn from the mitral valve leaflet 64 after the anchor 270 has been formed. The tether tails 280*a*, 280*b* extend proximally from the anchor 270. In some examples, the two tether tails 280*a*, 280*b* may extend from the proximal side of the leaflet 64, such as the side of the leaflet 64 oriented toward the left ventricle 3. The tether tails 280*a*, 280*b* can extend out of the heart 1 through the opening 40 formed in the ventricular wall. For example, the rigid elongate tube 710 can be slid/withdrawn over the tether tails 280*a*, 280*b*. The tether tails 280*a*, 280*b* can remain while the elongate rigid tube 710 is withdrawn from the left ventricle 3. The tether tails 280*a*, 280*b* can advantageously be tensioned to facilitate desired coaptation of the mitral valve leaflets. The tether tails 280*a*, 280*b* coupled to the anchor 270 may be secured at the desired tension using a surgical pad positioned over an externally oriented surface of the heart 1 as described herein. One or more knots (e.g., a knot stack) or other suture fixation mechanism(s) or device(s) may be implemented to hold the tether tails 280*a*, 280*b* at the desired tension and to the surgical pad. With the tether tails 280*a*, 280*b* fixed to the ventricle wall, a ventricular portion of the tether tails 280*a*, 280*b* may advantageously function as replacement leaflet cords (e.g., chordae tendineae) that are configured to tether the mitral valve leaflet 64 in a desired manner and at a desired tension.

Figure 9:
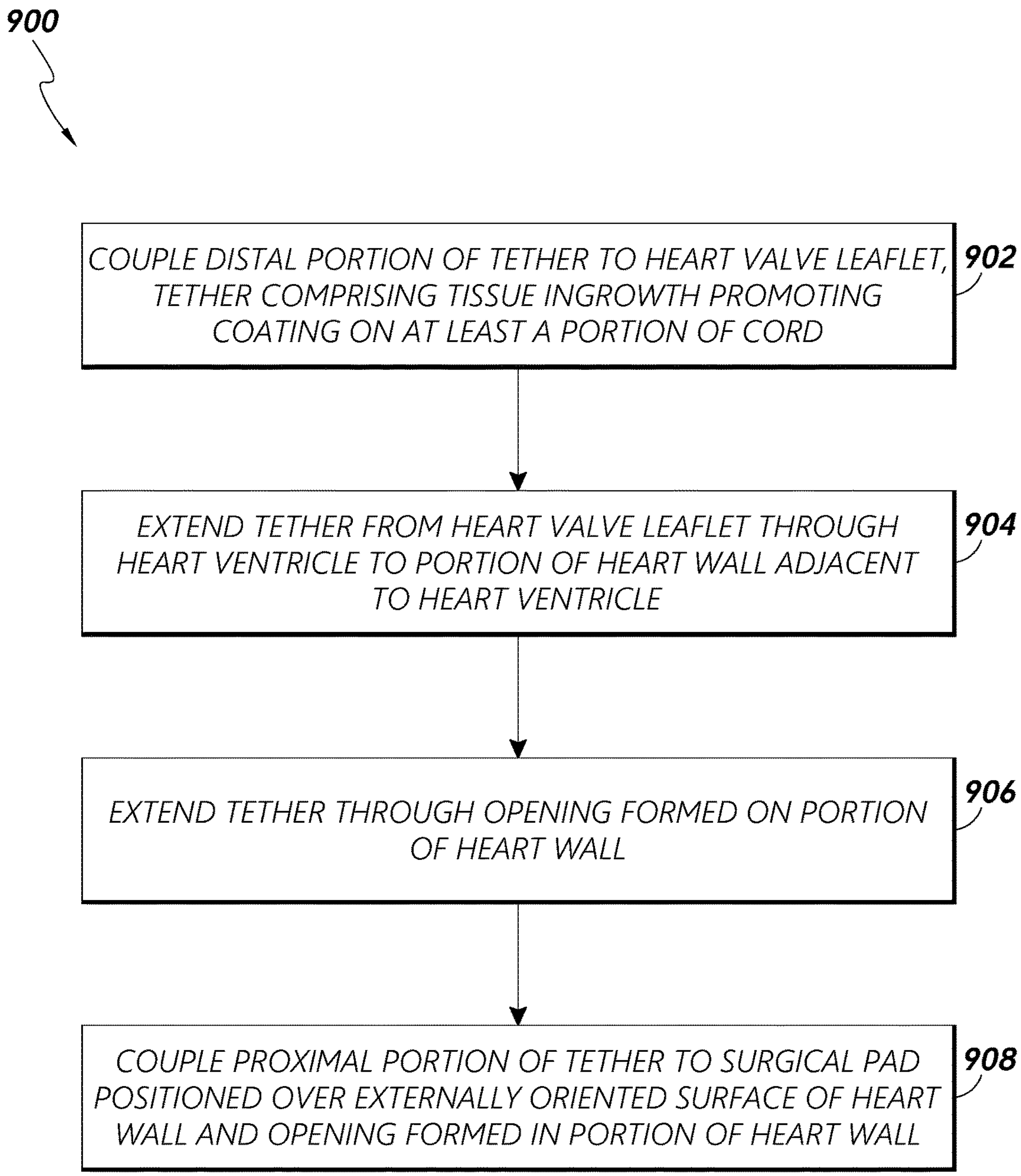
FIG. 9 is a flow diagram of an example of a process for deploying an artificial chordae system into a heart, according to some instances.

FIG. 9 is a process flow diagram of an example of a deployment process 900 for delivering an artificial chordae system as described herein to a target site. In block 902, the process can involve coupling a distal portion of a tether to a heart valve leaflet, the tether comprising a tissue ingrowth promoting coating over at least a portion of a cord. Coupling the distal portion of the tether to the heart valve leaflet can comprise providing an anchor on an atrial facing surface of the heart valve leaflet. Providing the anchor can comprise forming a bulky-knot anchor over the atrial facing surface of the heart valve leaflet using the tether.

The tether can comprise one or more characteristics described herein. In some instances, the cord can be biodegradable. For example, the cord can be a biodegradable polymeric suture. In some instances. The cord is non-biodegradable. For example, the cord can be an expanded polytetrafluorethylene (ePTFE) suture.

In block 904, the process an involve extending the tether from the heart valve leaflet through a heart ventricle to a portion of a heart wall adjacent to the heart ventricle, where the heart valve leaflet controls the flow of blood into and out of the heart ventricle. In block 906, the process can involve extending the tether through an opening formed on the portion of the heart wall. As described herein, an opening can be formed on a portion of the ventricular wall to allow access into the ventricle so as to deploy the tether onto the heart valve leaflet. An artificial chordae delivery system as described herein can be inserted into the ventricle through the opening to couple the distal portion of the tether to the heart valve leaflet.

In block 908, the process can involve coupling a proximal portion of the tether to a surgical pad positioned over an externally oriented surface of the heart wall and the opening formed in the portion of the heart wall. The surgical pad can comprise an antigen removal processed animal tissue, including a decellularized animal tissue. For example, the surgical pad can be an antigen removal processed animal tissue membrane, including a decellularized animal tissue membrane. The proximal portion of the tether can be coupled to the animal tissue membrane. Native tissue can migrate onto and grow on the antigen removal processed animal tissue membrane. The antigen removal processed animal tissue can be consumed and/or degrade over time. In some instances, the surgical pad can optionally comprise a tissue ingrowth promoting coating as described herein. For example, the tissue ingrowth coating can be over and/or on one or more surfaces of the antigen removal processed animal tissue membrane.

The biodegradable coating of the tether and/or the biodegradable coating of the surgical pad can comprise a protein, including an extracellular matrix (ECM) protein. The tissue ingrowth promoting coating of the surgical pad can be the same as or different from the tissue ingrowth promoting coating of the tether.

The surgical pad can be biodegradable. The surgical pad can be consumed and/or degrade as native heart tissue migrate onto and grow over the surgical pad. In some instances, the tether can be at least partially biodegradable. As described herein, the tether can comprise an anchor coupled to an elongate portion. The elongate portion and/or the anchor can be biodegradable. In some instances, the tether can be entirely biodegradable such that the tether is consumed and/or degrades as native tissue grow over the tether. Delivering the artificial chordae system as described herein to a target site can facilitate regenerating native tissue tethering for the heart valve leaflet.

ADDITIONAL EXAMPLES

Example 1: An artificial chordae system comprising:

a surgical pad configured to be externally positioned over an opening formed in a portion of a heart wall adjacent to a heart ventricle; and a tether comprising a cord and a tissue ingrowth promoting coating over at least a portion of the cord, the tether comprising a distal portion being configured to couple to a heart valve leaflet, the tether being dimensioned to extend from the heart valve leaflet through the heart ventricle to the opening in the heart wall, and through the opening in the heart wall, a proximal portion of the tether being configured to be coupled to the surgical pad, and the tissue ingrowth promoting coating being configured to promote native tissue growth over the cord to provide regenerated native tissue over the cord for coupling the heart valve leaflet to the heart wall.

Example 2: The system of example 1, wherein the surgical pad is biodegradable.

Example 3: The system of example 2, wherein the surgical pad comprises decellularized animal tissue.

Example 4: The system of example 3, wherein the surgical pad is a sheet of the decellularized animal tissue.

Example 5: The system of example 3 or 4, wherein the surgical pad comprises bovine tissue.

Example 6: The system of any one of examples 3 to 5, wherein the surgical pad comprises porcine tissue.

Example 7: The system of any one of examples 3 to 6, wherein the surgical pad comprises blood vessel tissue.

Example 8: The system of any one of examples 2 to 7, wherein the surgical pad comprises a second tissue ingrowth promoting coating over at least a portion of a decellularized animal tissue membrane.

Example 9: The system of example 8, wherein at least one of the tissue ingrowth promoting coating of the tether and the second tissue ingrowth promoting coating of the surgical pad comprises a protein.

Example 10: The system of example 9, wherein the protein comprises an extracellular matrix (ECM) protein.

Example 11: The system of example 10, wherein the protein comprises fibronectin.

Example 12: The system of example 10 or 11, wherein the protein comprises laminin.

Example 13: The system of any one of examples 10 to 12, wherein the protein comprises collagen.

Example 14: The system of any one of examples 9 to 13, wherein the protein comprises an insect protein.

Example 15: The system of any one of examples 9 to 14, wherein the protein comprises a spider protein.

Example 16: The system of any one of examples 9 to 15, wherein the protein comprises a synthetic animal protein.

Example 17: The system of any one of examples 1 to 16, wherein the cord comprises a biomimetic micropattern on at least a portion thereof.

Example 18: The system of example 17, wherein the biomimetic micropattern comprises a plurality of grooves.

Example 19: The system of any one of examples 1 to 18, wherein the cord is non-biodegradable.

Example 20: The system of example 19, wherein the cord is an expanded polytetrafluoroethylene (ePTFE) cord.

Example 21: The system of any one of examples 1 to 18, wherein the cord is biodegradable.

Example 22: The system of example 21, wherein the cord comprises a biodegradable polymer.

Example 23: The system of example 21 or 22, wherein the cord comprises a core portion and an outer layer portion surrounding the core portion, the core portion comprising a composition configured to have a degradation rate slower than that of the outer layer portion.

Example 24: The system of example 21 or 22, wherein the cord comprises a middle portion between a first end portion and a second end portion, the middle portion comprising a composition configured to have a degradation rate slower than that of the first and the second end portions.

Example 25: The system of any one of examples 1 to 24, wherein at least a portion of the tether extending between the heart valve leaflet and the portion of the heart wall comprises the tissue ingrowth promoting coating over the cord.

Example 26: The system of any one of examples 1 to 25, wherein the distal portion of the tether comprises an anchor configured to be positioned over a surface of the heart valve leaflet oriented away from the heart ventricle to couple the tether to the heart valve leaflet, the anchor comprising the tissue ingrowth promoting coating thereon.

Example 27: The system of example 26, wherein the anchor comprises a bulky-knot, the bulky-knot being formed using a portion of the tether.

Example 28: The system of any one of examples 1 to 27, wherein the surgical pad and the tether are sterilized.

Example 29: A tether comprising:

a cord; and a tissue ingrowth promoting coating over at least a portion of the cord, the tissue ingrowth promoting coating being configured to promote native tissue growth over the cord to provide regenerated native tissue over the cord for coupling a heart valve leaflet to a ventricular heart wall, the tether comprising a distal portion configured to couple to the heart valve leaflet, and the tether being configured to extend proximally from the heart valve leaflet through a heart ventricle to a portion of the ventricular heart wall to couple the heart valve leaflet to the ventricular heart wall.

Example 30: The tether of example 29, wherein the tissue ingrowth promoting coating comprises an extracellular matrix (ECM) protein Example 31: The tether of example 29 or 30, wherein the tissue ingrowth promoting coating comprises an insect protein.

Example 32: The tether of any one of examples 29 to 31, wherein the tissue ingrowth promoting coating comprises a spider protein.

Example 33: The tether of any one of examples 29 to 32, wherein the tissue ingrowth promoting coating comprises a synthetic animal protein.

Example 34: The tether of any one of examples 29 to 33, wherein the cord comprises a biomimetic micropattern on at least a portion thereof.

Example 35: The tether of any one of examples 29 to 34, wherein the cord is an expanded polytetrafluoroethylene (ePTFE) cord.

Example 36: The tether of any one of examples 29 to 34, wherein the cord comprises a biodegradable polymer.

Example 37: A method of deploying an artificial chordae system, the method comprising:

coupling a distal portion of a tether to a heart valve leaflet, the tether comprising a tissue ingrowth promoting coating over at least a portion of a cord;

extending the tether from the heart valve leaflet through a heart ventricle to a portion of a heart wall adjacent to the heart ventricle, the heart valve leaflet controlling blood flow into and out of the heart ventricle;

extending the tether through an opening formed on the portion of the heart wall; and coupling a proximal portion of the tether to a surgical pad positioned over an externally oriented surface of the heart wall and the opening formed in the portion of the heart wall.

Example 38: The method of example 37, wherein the surgical pad comprises decellularized animal tissue.

Example 39: The method of example 37 or 38, wherein the surgical pad comprises a second tissue ingrowth promoting coating on at least a portion thereof.

Example 40: The method of example 39, wherein at least one of the tissue ingrowth promoting coating of the tether and the second tissue ingrowth promoting coating of the surgical pad comprises an extracellular matrix (ECM) protein.

Example 41: The method of any one of examples 37 to 40, wherein the cord is biodegradable.

Example 42: The method of any one of examples 37 to 41, wherein coupling the distal portion of the tether to the heart valve leaflet comprises providing an anchor on an atrial facing surface of the heart valve leaflet.

Example 43: The method of example 42, wherein providing the anchor comprises forming a bulky-knot anchor over the atrial facing surface of the heart valve leaflet using the tether.

Depending on the example, certain acts, events, or functions of any of the processes or algorithms described herein can be performed in a different sequence, may be added, merged, or left out altogether. Thus, in certain instances, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain instances include, while other instances do not include, certain features, elements and/or steps. Thus, such conditional language is not generally intended to imply that features, elements and/or steps are in any way required for one or more instances or that one or more instances necessarily include logic for deciding, with or without author input or prompting, whether these features, elements and/or steps are included or are to be performed in any particular instance. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain instances require at least one of X, at least one of Y and at least one of Z to each be present.

It should be appreciated that in the above description of instances, various features are sometimes grouped together in a single instance, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular instance herein can be applied to or used with any other instance(s). Further, no component, feature, step, or group of components, features, or steps are necessary or indispensable for each instance. Thus, it is intended that the scope of the inventions herein disclosed and claimed below should not be limited by the particular instances described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example instances belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. An artificial chordae system comprising:

a surgical pad configured to be externally positioned over an opening formed in a portion of a heart wall adjacent to a heart ventricle; and a tether comprising a cord and a tissue ingrowth promoting coating over at least a portion of the cord, the tether comprising a distal portion being configured to couple to a heart valve leaflet, the tether being dimensioned to extend from the heart valve leaflet through the heart ventricle to the opening in the heart wall, and through the opening in the heart wall, a proximal portion of the tether being configured to be coupled to the surgical pad, and the tissue ingrowth promoting coating comprising a protein and being configured to promote native tissue growth over the cord to provide regenerated native tissue over the cord for coupling the heart valve leaflet to the heart wall, wherein the surgical pad is biodegradable and comprises decellularized animal tissue.

2. The system of claim 1, wherein the surgical pad comprises at least one of bovine tissue, porcine tissue, and blood vessel tissue.

3. The system of claim 1, wherein the surgical pad comprises a second tissue ingrowth promoting coating over at least a portion of a decellularized animal tissue membrane.

4. The system of claim 3, wherein the second tissue ingrowth promoting coating of the surgical pad comprises a protein.

5. The system of claim 1, wherein the protein comprises at least one of an extracellular matrix (ECM) protein, insect protein, spider protein and synthetic animal protein.

6. The system of claim 5, wherein the extracellular matrix (ECM) protein comprises at least one of fibronectin, laminin, and collagen.

7. The system of claim 1, wherein the cord comprises a biomimetic micropattern on at least a portion thereof.

8. The system of claim 1, wherein the cord is an expanded polytetrafluoroethylene (ePTFE) cord.

9. The system of claim 1, wherein the cord comprises a biodegradable polymer.

10. The system of claim 9, wherein the cord comprises a middle portion between a first end portion and a second end portion, the middle portion comprising a composition configured to have a degradation rate slower than that of the first and the second end portions.

11. The system of claim 1, wherein the tissue ingrowth promoting coating covers the entire tether.

12. An artificial chordae system comprising:

a surgical pad configured to be externally positioned over an opening formed in a portion of a heart wall adjacent to a heart ventricle; and a tether comprising a cord and a tissue ingrowth promoting coating over at least a portion of the cord, the tether comprising a distal portion being configured to couple to a heart valve leaflet, the tether being dimensioned to extend from the heart valve leaflet through the heart ventricle to the opening in the heart wall, and through the opening in the heart wall, a proximal portion of the tether being configured to be coupled to the surgical pad, and the tissue ingrowth promoting coating comprising a protein and being configured to promote native tissue growth over the cord to provide regenerated native tissue over the cord for coupling the heart valve leaflet to the heart wall, wherein the cord comprises a biomimetic micropattern on at least a portion thereof, wherein the biomimetic micropattern comprises a plurality of grooves.

13. The system of claim 12, wherein the protein comprises at least one of an extracellular matrix (ECM) protein, insect protein, spider protein and synthetic animal protein.

14. The system of claim 13, wherein the extracellular matrix (ECM) protein comprises at least one of fibronectin, laminin, and collagen.

15. The system of claim 12, wherein the surgical pad is biodegradable.

16. The system of claim 15, wherein the surgical pad comprises decellularized animal tissue.

17. An artificial chordae system comprising:

a surgical pad configured to be externally positioned over an opening formed in a portion of a heart wall adjacent to a heart ventricle; and a tether comprising a cord and a tissue ingrowth promoting coating over at least a portion of the cord, the tether comprising a distal portion being configured to couple to a heart valve leaflet, the tether being dimensioned to extend from the heart valve leaflet through the heart ventricle to the opening in the heart wall, and through the opening in the heart wall, a proximal portion of the tether being configured to be coupled to the surgical pad, and the tissue ingrowth promoting coating comprising a protein and being configured to promote native tissue growth over the cord to provide regenerated native tissue over the cord for coupling the heart valve leaflet to the heart wall, wherein the cord comprises a biodegradable polymer and further comprises a core portion and an outer layer portion surrounding the core portion, the core portion comprising a composition configured to have a degradation rate slower than that of the outer layer portion.

18. The system of claim 17, The system of claim 1, wherein the cord comprises a biomimetic micropattern on at least a portion thereof.

19. The system of claim 17, wherein the surgical pad is biodegradable.

20. The system of claim 19, wherein the surgical pad comprises decellularized animal tissue.

* * * * *